(12) United States Patent
da Costa e Silva et al.

(10) Patent No.: US 7,223,903 B2
(45) Date of Patent: May 29, 2007

(54) PROTEIN KINASE STRESS-RELATED PROTEINS AND METHODS OF USE IN PLANTS

(76) Inventors: Oswaldo da Costa e Silva, 203 Littleford La., Cary, NC (US) 27519; Manabu Ishitani, 202 Wagon Trail Dr., Cary, NC (US) 27513; Stefan Henkes, Karl-Liebknecht Str. 110, D-14482, Potsdam (DE); Nocha van Thielen, 6123 Farrington Rd., Apt. 07, Chapel Hill, NC (US) 27517; Ruoying Chen, 105 Rustic Pine Ct., Apex, NC (US) 27502

( * ) Notice: Subject to any disclaimer, the term of this patent is extended or adjusted under 35 U.S.C. 154(b) by 307 days.

(21) Appl. No.: 10/168,844

(22) PCT Filed: Dec. 22, 2000

(86) PCT No.: PCT/US00/34970

§ 371 (c)(1),
(2), (4) Date: Nov. 18, 2002

(87) PCT Pub. No.: WO01/45492

PCT Pub. Date: Jun. 28, 2001

(65) Prior Publication Data

US 2003/0217392 A1    Nov. 20, 2003

Related U.S. Application Data

(60) Provisional application No. 60/171,745, filed on Dec. 22, 1999.

(51) Int. Cl.
    C12N 15/82    (2006.01)
    C12N 15/29    (2006.01)
(52) U.S. Cl. ...................... 800/289; 536/23.6
(58) Field of Classification Search ............... 536/23.6; 800/289
    See application file for complete search history.

(56) References Cited

U.S. PATENT DOCUMENTS 5,977,442 A * 11/1999 Klessig et al. .............. 800/301

FOREIGN PATENT DOCUMENTS

| EP | 1 078 985 A2 | 2/2001 |
|---|---|---|
| WO | WO 98/26045 | 6/1998 |
| WO | WO 99/54489 | 10/1999 |
| WO | WO 00/06706 | 2/2000 |
| WO | WO 00/09724 | 2/2000 |
| WO | WO 01/02541 A2 | 1/2001 |

OTHER PUBLICATIONS

Banno H. et al. NPK1, a tobacco gene that encodes a protein with a domain homologous to yeast BCK1, STE11, and Byr2 protein kinases. Mol Cell Biol. Aug. 1993; 13(8):4745-52.*
Whisstock J.C. et al. Prediction of protein function from protein sequence and structure. Q Rev Biophys. Aug. 2003;36(3):307-40. Review.*
Van Camp W. et al. Enhancement of oxidative stress tolerance in transgenic tobacco plants overproducing Fe-superoxide dismutase in chloroplasts. Plant Physiol. Dec. 1996;112(4):1703-14.*
Sandler S.J. et al. Inhibition of gene expression in transformed plants by antisense RNA. Plant Molecular Biology, 1988, vol. 11, No. 3, pp. 301-310.*
van der Krol A.R. et al. Inhibition of flower pigmentation by antisense CHS genes: promoter and minimal sequence requirements for the antisense effect. Plant Mol Biol. Apr. 1990;14(4):457-66.*
Waterhouse et al. Virus resistance and gene silencing: killing the messenger. Trends Plant Sci. Nov. 1999;4(11):452-457.*
Becraft, P.W., "Receptor Kinases in Plant Development", 1998, Trends in Plant Science, 3:384-388.
Bush, D.S., "Calcium Regulation in Plant Cells and Its Roll in Signaling", 1995, Annu. Rev. Plant Physiol. Plant Mol. Biol., 46:95-122.
Jonak, C. et al., "Stress signaling in plants: A mitogen-activated protein kinase pathway is activated by cold and drought", 1996, Proc. Natl. Acad. Sci., vol. 93, pp. 11274-11279.
Knight, M.R. et al., "Transgenic Plant Aequorin Reports the Effects of Touch and Cold-Shock and Elicitors on Cytoplasmic Calcium", 1991, Nature, 352:524-526.
Kovtun, Y. et al., "Functional analysis of oxidative stress-activated mitogen-activated protein kinase cascade in plants", 2000, PNAS, vol. 97, No. 6, pp. 2940-2945.

(Continued)

Primary Examiner—Cynthia Collins
(74) Attorney, Agent, or Firm—Elaine Sale; Mark Westhafer; Ruoying Chen

(57) ABSTRACT

A transgenic plant transformed by a protein kinase stress-related protein (PKSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated PKSRP, and isolated nucleic acid coding PKSRP, and vectors and host cells containing the latter. Further provided are methods of producing transgenic plants expressing PKSRP, and methods of identifying novel PKSRP and methods of modifying the expression of PKSRP in plants.

18 Claims, 11 Drawing Sheets

OTHER PUBLICATIONS

Lee, J. H. et al., "A highly conserved kinase is an essential component for stress tolerance in yeast and plant cells", 1999, Proc. Natl. Acad. Sci., vol. 96, pp. 5873-5877.

Li, Z. & Wurtzel, Sequence Listing Accession No. 081105 for Leucine-Rich Repeat Transmembrane Protein Kinase 1 (fragment) Nov. 1, 1998.

Liu, J. et al., "The Arabidopsis thaliana *SOS2* gene encodes a protein kinase that is required for salt tolerance", 2000, PNAS, vol. 97, No. 7, pp. 3730-3734.

Machuka, J. et al., "Sequence Analysis of Expressed Sequence Tags from an ABA-Treated cDNA library Identifies Stress Response Genes in the Moss Physcomitrella patens", 1999, Plant Cell Physiol. 40(4):378-387.

Munnik, T. and Meijer, H.J.G., "Osmotic stress activates distinct lipid and MAPK signalling pathways in plants", 2001, FEBS Letters, vol. 498, pp. 172-178.

Pardo, J. M. et al., "Stress signaling through $Ca^{2+}$/calmodulin-dependent protein phosphatase calcineurin mediates salt adaptation in plants", 1998, Proc. Natl. Acad. Sci., vol. 95, pp. 9681-9686.

Saijo, Y. et al., "Over-expression of a single $Ca^{2+}$-dependent protein kinase confers both cold and salt/drought tolerance on rice plants", 2000, The Plant Journal, vol. 23, No. 3, pp. 319-327.

Schroeder, J.I. and Thuleau, P., "$Ca^{2+}$ Channels in Higher Plant Cells", 1991, The Plant Cell, 3:555-559.

Shinozaki, K. and Yamaguchi-Shinozaki K., "Gene Expression and Signal Transduction in Water-Stress Response", 1997, Plant Physiol., vol. 115, pp. 327-334.

Urao, T. et al., "Two Genes that Encode $Ca^{2+}$-Dependent Protein Kinases are Induced by Drought and High-Salt Stresses in Arabidopsis Thaliana", 1994, Mol. Gen. Genet., 244:331-340.

Van der Geer and Hunter, T., "Receptor Protein-Tyrosine Kinases and Their Signal Transduction Pathways", 1994, Annu. Rev. Cell. Biol., 10:251-337.

Winicov, I., "New Molecular Approaches to Improving Salt Tolerance in Crop Plants", 1998, Annals of Botany, vol. 82, pp. 703-710.

* cited by examiner

FIGURE 1A

Nucleotide sequence of the partial PK-1 from *Physcomitrella patens* (SEQ ID NO:1)

GCACGAGGACAAGGGCTACTCTGGGGCTACTGCCGATTTGTGGTCATGCGGTGTTAT

TTTATATGTACTGATGGCTGGATACTTGCCATTTGAGGAGCCCACAATCATGGCACT

TTACAAGAAGATTTACCGAGCACAGTTCTCTTGGCCTCCTTGGTTCTCGTCAGGAGC

CCGGAAATTAATCTCAAAGATACTGGATCCCAATCCAAGAACTCGCATTTCTGCATC

TCAAATTTATAAAAATGATTGGTTTAAGAAAGGATATACTCCAGCCCAGTTTGACAG

AGAAGTTGATGTCAACCTTGACGATGTGAATGCTATCTTTA

FIGURE 1B

Nucleotide sequence of the partial PK-2 from *Physcomitrella patens* (SEQ ID NO:2)

GCACCAGGTCCTCTACATGCTTATTTCAACCCTAAACCTGAAGGGTCATTATTATCA

GGAAGTATGGCAAGCTCTACAACGATTTCTTATGGATCTAGCATGGCCAACTACACA

TGCACTGCTAAGACGTTCACTTTAGCAGAATTAGAAAGAGCAACAGATAATTTTAGA

CCTGATAATGTAGTCGGCGAAGGGGGCTTTGGTCGAGTTTACCAAGGGGTACTTGAT

AGTGGTATTGAAGTGGCTGTAAAGGTGCTGACAAGGGATGATCATGAGGGTGGTCG

TGAGTTTGTTGCGGAGGTANAAATGTTAAGCAGATTGCACCATCGCAACCTTGTGAA

GCTAATTGGCATCTGTACTGAGGAAATACGATGTTTGGTTTATGAGCTCATCACGAA

CGGGAGCGTGGAATCTCACTTGCATGGTCTAGATAAATACACTGCTCCTCTCAACTG

GGATGCACGTGTT

FIGURE 1C

Nucleotide sequence of the partial MPK-1 from *Physcomitrella patens* (SEQ ID NO:3)

GCACGAGGTGACCTGAAGCCCAGTAATCTCCTCATCAATTGCAACGACTGTCTACTC

AAGATTTGTGATTTTGGCTTGGCTCGAACATCTGCAGAGGATGACTTCCTTACGGAG

TATGTTGTTACTCGACCATATCGAGCTCCAGAGCTCTTGCTTGGGAGCCGAATGTAC

ACAGCGGCTGTTGATATGTGGTCAGTGGGCTGCATCTTCATGGAGATGCTTACAGGA

CAACCTTTGTTTCCAATCCGGTCAAGGCAAGAGCATCCCGTGAATCATTTGAAACTC

ATCACGGAGCTTCTAGGAACACCCGATGCTTCGGACCTGTCGTTTCTGCAGAATCCA

GATGCTCGGCAAAGAATCCAAATGGCTTTGTTAGGTCAGGAAAGGAAGCCTTTGTTT

TCGAGGTTTCCTCAAACGTCTGCAATAGCTTGTGACTTAGCGGAGAAGATGCTGAGG

TTTAACCCATCCAACAGAATAACTGCGGAAGAGGCTTGGCCCATCCTTACTTGGGCA

GCGCTTCACGACCTAAGTGATGAGCCAACGTGTCATCTTATGTTCGAC

FIGURE 2A

Nucleotide sequence of the full-length PK-1 from *Physcomitrella patens* (SEQ ID NO:4)

ATCCCGGGCGTTCAAGCAGGTGAATATGACAACTAAATCAAACATGCCGACTACTA

ACGTCGAACGTACGCGGGTCGGAAAGTATGACCTCGGCAAGACCTTGGGAGAGGGT

ACATTTGCCAAAGTCAAGGTGGCCAAACATATTGACACTGGTCACACTGTTGCCATC

AAGATTTTGGACAAGGAGAAGATTCTCAGGCACAAGATGGTGGAACAGATCAAAAG

AGAAATATCTACCATGAAGCTGGTGAAACATCCCTATGTCGTCCAGCTGTTGGAGGT

AATGGCCAGCAGGACGAAGATCTACATTGTGCTTGAGTATGTCACAGGTGGCGAGC

TTTTTAATAAGATTGCTCAACAAGGAAGACTGTCAGAGGATGAAGCAAGGAAGTAT

TTTCAGCAGCTGATTGATGCAGTTGATTATTGCCACAGTCGGCAAGTGTATCACAGA

GATCTGAAACCAGAGAATCTTCTTCTGGATTCCAAAGGCAACTTAAAAATTTCCGAC

TTTGGCTTGAGTGCGCTACCTCAGCAATTTAGGGAAGATGGTTTATTACATACAACT

TGCGGAACTCCCAACTACGTGGCCCCTGAGGTTATCATGGACAAGGGCTACTCTGGG

GCTACTGCCGATTTGTGGTCATGCGGTGTTATTTTATATGTACTGATGGCTGGATACT

TGCCATTTGAGGAGCCCACAATCATGGCACTTTACAAGAAGATTTACCGAGCACAGT

TCTCTTGGCCTCCTTGGTTCTCGTCAGGAGCCCGGAAATTAATCTCAAAGATACTGG

ATCCCAATCCAAGAACTCGCATTTCTGCATCTCAAATTTATAAAAATGATTGGTTTA

AGAAAGGATATACTCCAGCCCAGTTTGACAGAGAAGTTGATGTCAACCTTGACGAT

GTGAATGCTATCTTTAGTTGCTCACAGGAACATATGGTTGTCGAAAGGAAGGAAAC

AAAGCCGGTGTCAATGAATGCTTTCGAGCTTATCTCCATGTCATCAGGGCTCAACCT

CTCCAGCCTCTTCGAGACGAAAGAGATTCCTGAAAAGGAGGACACTAGGTTTACGA

GTAAGAAGTCTGCGAAGGAGATCATCTCTTCAATTGAGGAAGCTGCAAAGCCCTTA

GGGTTCAACGTTTTGAAACGTGATTTCAAGCTGAAACTACAAGGTCAGCTGGGGAG

GAAGGGACCTCTGTCAGTTTCAACTGAGGTGTTTGAGGTGGCACCTTCTCTTTACAT

GGTTGAGTTACAGAAGAACAGCGGCGATACGTTGGAGTACAATAACTTTTATAAGA

ATCTTTCCAAGGGTCTCAAAGACATCGTGTGGAAAGCAGACCCTATTCCTACAAGTG

AGCAAAAGTAGAAAGCTTCCGCTACGGCTTTAATATATGCCCGTGCTGTGAAGTGCC

CGAGCTCAT

FIGURE 2B

Nucleotide sequence of the full-length PK-2 from *Physcomitrella patens* (SEQ ID NO:5)

ATCCCGGGCGCGCACAATTTCAGTTGGGAATCAAGCTGGAAAAGTTTTTTCCTCTAG

TGGCTGAGCTGGCCAAGGAACTGGCCATTGGACTCTTCTTACAAACTAGTCAAGTCC

GTATTGTAGGAGCCAATGCTGTTGAACCCAACCAGGACAAGACAAACGTGAGTGCA

GATTTTGTGCCGCTAGATACCAAATTTGATCACACCACTGCCCATCTTCTTGCTACAC

GCTTGTGGAGTGGTGAAGTTCCATTGAACAAGACACTATTTGGAACCTACTATGTTA

TTTATATAATTTACCCAGGTCTTCCTCCCTCTCCACCTCCCCAGTTCCCTGGGAATAT

TTCACCTTCAGGTCCTGTCAACCAGCTTCCATCTGGGGTGGATCCAAATAAAACAAA

TCATAAACTCAGTTCGGGAATGATTACCGTGATTGCTTTGGCTTCGGTTATGGGTGT

ATTGTTATTTATTGGGATTGTATGGCTCATTCTCCTACGCCGCAGCCTGGATGAGAA

AACTTCGCCTTCGGTTGTCGGTCCTCTACATGCTTATTTCAACCCTAAACCTGAAGGT

```
GTGCAACTGATCCAACTGAGAATGAATGCTTATTTCAACTCTAAACCTGAAGGGTCA

TTATTATCAGGAAGTATGGCAAGCTCTACAACGATTTCTTATGGATCTAGCATGGCC

AACTACACATGCACTGCTAAGACGTTCACTTTAGCAGAATTAGAAAGAGCAACAGA

TAATTTTAGACCTGATAATGTAGTCGGCGAAGGGGGCTTTGGTCGAGTTTACCAAGG

GGTACTTGATAGTGGTATTGAAGTGGCTGTAAAGGTGCTGACAAGGGATGATCATG

AGGGTGGTCGTGAGTTTGTTGCGGAGGTAGAAATGTTAAGCAGATTGCACCATCGC

AACCTTGCGAAGCTAATTGGCATCTGTACTGAGGAAATACGATGTTTGGTTTATGAG

CTCATCACGAACGGGAGCGTGGAATCTCACTTGCATGGTCTAGATAAATACACTGCT

CCTCTCAACTGGGATGCACGTGTTAAAATTGCATTAGGAGCTGCTCGTGGGCTGGCA

TACCTGCACGAAGATTCTCAGCCTAGGGTTATTCATAGAGATTTTAAAGGAAGCAAC

ATTCTACTTGAGGACGATTACACTCCAAAAGTATCTGATTTTGGTCTAGCTAAATCG

GCAACTGAGGGAGGCAAGGAGCATATTTCCACTCGAGTAATGGGCACGTTTGGATA

TGTGGCTCCTGAATACGCAATGACAGGACATTTGCTTGTGAAGAGTGACGTTTATAG

TTATGGAGTGGTACTGCTCGAGCTCCTCTCGGGGCGTAAACCCGTGGATATGTCTCA

ACCACCTGGACAAGAGAATCTAGTTACTTGGGCACGCCCACTCCTTACAAGCAAGG

ATGGACTAGAGCAGCTTGTGGATCCTTACCTCAAAGACAACTTTCCATTTGACCACT

TTGCGAAGGTAGCTGCAATAGCGTCCATGTGTGTACAACCTGAAGTCTCTCATCGAC

CATTCATGGGCGAGGTGGTGCAGGCCTTGAAACTTGTGTGCAATGAAACAGAAGCC

AAAGACGTCGGACAGGCTAAAGGAACAGTTCTCCCACTTCTGACTTGGCCGAAAC

ACAGAACACAGGATTTCTGCGGGACGCCACCTTTATTAGTGTTGATTACGACTCGGG

GCCCTTCGAAACCTTGGATCTTGAACAGCGAAAGCGGAAACCTCTTTCTGCTTCGGC

TACTATGAGTGGCTCTGGAGGGTTCTTACGACAACTTTCGGATTCATTCAGACGCTA

CAGTGTTTCTGCCCCTCCAAAGGCTGCTTCACTGCCAAGAACTTCATGGTATGCACT

GGGTAGTTCAAAACCTGTAGGAAGCATGAGTGAGGCTAGAGCAGCTAGATTCTTAG
```

ATCCTCAACGCAGGAGATTTTACGGGTTTTGGCCCTAATTCTTCCACGCCTGTTTTGA
CCTTTGCGGGCGTTAACGCAA

–FIGURE 2C

Nucleotide sequence of the full-length MPK-1 from *Physcomitrella patens* (SEQ ID NO:6)

ATCCCGGGCGGTTTGGACACGATGTTCCAGTCCTTTATATATATGAGACACAGCTGG
AGAAAACAGTGCAAGGGAAAGGTCTTGGAAAGTTTTTAATGCAGTTACTTGAGTTG
GTTGCACGAAAGAACAACATGAAAGCAGTACTTTTAGCTGTGCATAAAAGAAACAC
AAGGGCGCTAACCTTTTACAATGAACGTTTAGGGTATAAGTTGGCAATTAGATCAGC
ATCAAGTCAACAAAGCACACAAACTGTCACAGAGATGAAATACGAGATTCTTTGTA
AAACTTTCGATGTGGAGTACACAGCCGTTGTAGAGGAACGGCAAGGGGACATGGAT
TGTGAATCACGTGAAGAGAGCGCTGGAGAAGCAAGCTGCCAGACAGTTGACGCAGA
GGATCAGGTTTTGGATGACTCACGTCCTGATACAGAATGTGAGTCACGGATCGAGA
GCGTGCCAAACACCCTACAAGGAATGAAGTACACACAGTACAATGTGAGGGGCGAC
AAGTTTGAAGTCTACGACAAGTATGTAATGATTGGTCCCATTGGTCATGGAGCTTAT
GGCGATGTGTGTGCTTTCACGAACAGGGAGACAGGGGAGAAAGTGGCCATAAAGAA
GATTGGAAACGCATTTCAGAACAATACTACAGCGAGGCGCACACTTAGAGAGATTT
TGTTGCTCCGCCATACTGAACACGACAACATCATTCCCATCAGAGATATCATTGTGC
CTGCTAACATTGAGGACTTTCATGATGCCTATATCGCAAATGAGCTCATGGATACAG
ACCTTCACCAGATAGTGAGGTCAACAAAACTTGACGAATACCATTGCCAGTTCCTGC
TTTACCAGCTGTTGAGGGGTCTCAAATACATCCACTCTGCCAATATATTGCACCGTG
ACCTGAAGCCCAGTAATCTCCTCATCAATTGCAACGACTGTCTACTCAAGATTTGTG
ATTTTGGCTTGGCTCGAACATCTGCAGAGGATGACTTCCTTACGGAGTATGTTGTTA
CTCGACCATATCGAGCTCCAGAGCTCTTGCTTGGGAGCCGAATGTACACAGCGGCTG
TTGATATGTGGTCAGTGGGCTGCATCTTCATGGAGATGCTTACAGGACAACCTTTGT

TTCCAATCCGGTCAAGGCAAGGGCATCCCGTGAATCATTTGAAACCCATCACGGAG

CTTCTAGGAACACCCGATGCTTCGGACCTGTCGTTTCTGCAGAATCCAGATGCTCGG

CAAAGAATCCAAATGGCTTTGTTAGGTCAGGAAAGGAAGCCTTTGTTTTCGAGGTTT

CCTCAAACGTCTGCAATAGCTTGTGACTTAGCGGAGAAGATGCTGAGGTTTAACCCA

TCCAACAGAATAACTGCGGAAGAGGCCTTGGCCCATCCTTACTTGGCAGCGCTTCAC

GACCTAAGTGATGAGCCAACGTGTCATCTTATGTTCGACTTCGATGCTTACCTTCCCA

GCCTAACAGTTGAGCATGTGAAAACTCTTATCTGGAGGGAAGCTACACTTATCAACG

TCCAGTAATCGCCATAAAGATGTATCGGACCAGATGTCGCTGCACCAATTGGCAAA

GCTTAAGGGTTGAGGGACTTAAACGCGGTTAGTTAACGCAA

FIGURE 3A

Deduced amino acid sequence of PK-1 from *Physcomitrella patens* (SEQ ID NO:7)

MPTTNVERTRVGKYDLGKTLGEGTFAKVKVAKHIDTGHTVAIKILDKEKILRHKMVEQI
KREISTMKLVKIIPYVVQLLEVMASRTKIYIVLEYVTGGELFNKIAQQGRLSEDEARKYF
QQLIDAVDYCHSRQVYHRDLKPENLLLDSKGNLKISDFGLSALPQQFREDGLLHTTCGT
PNYVAPEVIMDKGYSGATADLWSCGVILYVLMAGYLPFEEPTIMALYKKIYRAQFSWPP
WFSSGARKLISKILDPNPRTRISASQIYKNDWFKKGYTPAQFDREVDVNLDDVNAIFSCS
QEHMVVERKETKPVSMNAFELISMSSGLNLSSLFETKEIPEKEDTRFTSKKSAKEIISSIEE
AAKPLGFNVLKRDFKLKLQGQLGRKGPLSVSTEVFEVAPSLYMVELQKNSGDTLEYNN
FYKNLSKGLKDIVWKADPIPTSEQK*

FIGURE 3B

Deduced amino acid sequence of PK-2 from *Physcomitrella patens* (SEQ ID NO:8)

MITVIALASVMGVLLFIGIVWLILLRRSLDEKTSPSVVGPLHAYFNPKPEGVQLIQLRMN
AYFNSKPEGSLLSGSMASSTTISYGSSMANYTCTAKTFTLAELERATDNFRPDNVVGEG
GFGRVYQGVLDSGIEVAVKVLTRDDHEGGREFVAEVEMLSRLHHRNLAKLIGICTEEIR

CLVYELITNGSVESHLHGLDKYTAPLNWDARVKIALGAARGLAYLHEDSQPRVIHRDFK
GSNILLEDDYTPKVSDFGLAKSATEGGKEHISTRVMGTFGYVAPEYAMTGHLLVKSDV
YSYGVVLLELLSGRKPVDMSQPPGQENLVTWARPLLTSKDGLEQLVDPYLKDNFPFDH
FAKVAAIASMCVQPEVSHRPFMGEVVQALKLVCNETEAKDVGQAKGTVSPTSDLAETQ
NTGFLRDATFISVDYDSGPFETLDLEQRKRKPLSASATMSGSGGFLRQLSDSFRRYSVSA
PPKAASLPRTSWYALGSSKPVGSMSEARAARFLDPQRRRFYGFWP*

FIGURE 3C

Deduced amino acid sequence of MRK-1 from *Physcomitrella patens* (SEQ ID NO:9)

MQLLELVARKNNMKAVLLAVHKRNTRALTFYNERLGYKLAIRSASSQQSTQTVTEMK
YEILCKTFDVEYTAVVEERQGDMDCESREESAGEASCQTVDAEDQVLDDSRPDTECESR
IESVPNTLQGMKYTQYNVRGDKFEVYDKYVMIGPIGHGAYGDVCAFTNRETGEKVAIK
KIGNAFQNNTTARRTLREILLLRHTEHDNIIPIRDIIVPANIEDFHDAYIANELMDTDLHQI
VRSTKLDEYHCQFLLYQLLRGLKYIHSANILHRDLKPSNLLINCNDCLLKICDFGLARTS
AEDDFLTEYVVTRPYRAPELLLGSRMYTAAVDMWSVGCIFMEMLTGQPLFPIRSRQGH
PVNHLKPITELLGTPDASDLSFLQNPDARQRIQMALLGQERKPLFSRFPQTSAIACDLAEK
MLRFNPSNRITAEEALAHPYLAALHDLSDEPTCHLMFDFDAYLPSLTVEHVKTLIWREA
TLINVQ*

FIGURE 4

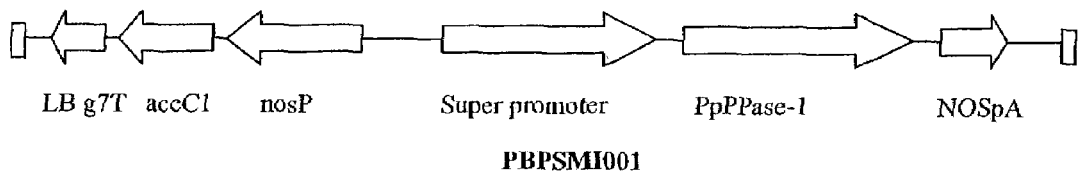

PBPSMI001

SEQUENCE LISTING

<160> NUMBER OF SEQ ID NOS: 28

<210> SEQ ID NO 1
<211> LENGTH: 326
<212> TYPE: DNA
<213> ORGANISM: Physcomitrella patens

<400> SEQUENCE: 1

```
gcacgaggac aagggctact ctggggctac tgccgatttg tggtcatgcg gtgttatttt      60
atatgtactg atggctggat acttgccatt tgaggagccc acaatcatgg cactttacaa     120
gaagatttac cgagcacagt tctcttggcc tccttggttc tcgtcaggag cccggaaatt     180
aatctcaaag atactggatc ccaatccaag aactcgcatt tctgcatctc aaatttataa     240
aaatgattgg tttaagaaag gatatactcc agcccagttt gacagagaag ttgatgtcaa     300
ccttgacgat gtgaatgcta tcttta                                          326
```

<210> SEQ ID NO 2
<211> LENGTH: 468
<212> TYPE: DNA
<213> ORGANISM: Physcomitrella patens
<220> FEATURE:
<221> NAME/KEY: modified_base
<222> LOCATION: (1)..(468)
<223> OTHER INFORMATION: "n" represents a, t, c, g, other or unknown

<400> SEQUENCE: 2

```
gcaccaggtc ctctacatgc ttatttcaac cctaaacctg aagggtcatt attatcagga      60
agtatggcaa gctctacaac gatttcttat ggatctagca tggccaacta cacatgcact    120
gctaagacgt tcactttagc agaattagaa agagcaacag ataattttag acctgataat    180
```

```
gtagtcggcg aaggggcctt tggtcgagtt taccaagggg tacttgatag tggtattgaa      240
gtggctgtaa aggtgctgac aagggatgat catgagggtg gtcgtgagtt tgttgcggag      300
gtanaaatgt taagcagatt gcaccatcgc aaccttgtga agctaattgg catctgtact      360
gaggaaatac gatgtttggt ttatgagctc atcacgaacg ggagcgtgga atctcacttg      420
catggtctag ataaatacac tgctcctctc aactgggatg cacgtgtt                   468

<210> SEQ ID NO 3
<211> LENGTH: 561
<212> TYPE: DNA
<213> ORGANISM: Physcomitrella patens

<400> SEQUENCE: 3
gcacgaggtg acctgaagcc cagtaatctc ctcatcaatt gcaacgactg tctactcaag       60
atttgtgatt ttggcttggc tcgaacatct gcagaggatg acttccttac ggagtatgtt      120
gttactcgac catatcgagc tccagagctc ttgcttggga gccgaatgta cacagcggct      180
gttgatatgt ggtcagtggg ctgcatcttc atggagatgc ttacaggaca acctttgttt      240
ccaatccggt caaggcaaga gcatcccgtg aatcatttga aactcatcac ggagcttcta      300
ggaacacccg atgcttcgga cctgtcgttt ctgcagaatc cagatgctcg gcaaagaatc      360
caaatggctt tgttaggtca ggaaaggaag ccttgtttt cgaggtttcc tcaaacgtct      420
gcaatagctt gtgacttagc ggagaagatg ctgaggttta acccatccaa cagaataact      480
gcggaagagg cttggcccat ccttacttgg gcagcgcttc acgacctaag tgatgagcca      540
acgtgtcatc ttatgttcga c                                                561

<210> SEQ ID NO 4
<211> LENGTH: 1424
<212> TYPE: DNA
<213> ORGANISM: Physcomitrella patens

<400> SEQUENCE: 4
atcccgggcg ttcaagcagg tgaatatgac aactaaatca acatgccga ctactaacgt        60 cgaacgtacg cgggtcggaa agtatgacct cggcaagacc ttgggagagg gtacatttgc      120
caaagtcaag gtggccaaac atattgacac tggtcacact gttgccatca agattttgga      180
caaggagaag attctcaggc acaagatggt ggaacagatc aaaagagaaa tatctaccat      240
gaagctggtg aaacatccct atgtcgtcca gctgttggag gtaatggcca gcaggacgaa      300
gatctacatt gtgcttgagt atgtcacagg tggcgagctt tttaataaga ttgctcaaca      360
aggaagactg tcagaggatg aagcaaggaa gtatttttcag cagctgattg atgcagttga      420
ttattgccac agtcggcaag tgtatcacag agatctgaaa ccagagaatc ttcttctgga      480
ttccaaaggc aacttaaaaa tttccgactt tggcttgagt gcgctacctc agcaatttag      540
ggaagatggt ttattacata caacttgcgg aactcccaac tacgtggccc tgaggttat      600 catggacaag ggctactctg ggctactgc cgatttgtgg tcatgcggtg ttatttttata      660 tgtactgatg gctggatact tgccatttga ggagcccaca atcatggcac tttcaagaa      720 gatttaccga gcacagttct cttggcctcc ttggttctcg tcaggagccc ggaaattaat      780
ctcaaagata ctggatccca atccaagaac tcgcatttct gcatctcaaa tttataaaaa      840
tgattggttt aagaaaggat atactccagc ccagtttgac agagaagttg atgtcaacct      900
tgacgatgtg aatgctatct ttagttgctc acaggaacat atggttgtcg aaaggaagga      960
aacaaagccg gtgtcaatga atgctttcga gcttatctcc atgtcatcag ggctcaacct     1020
```

-continued

| | |
|---|---|
| ctccagcctc ttcgagacga aagagattcc tgaaaaggag gacactaggt ttacgagtaa | 1080 |
| gaagtctgcg aaggagatca tctcttcaat tgaggaagct gcaaagccct tagggttcaa | 1140 |
| cgttttgaaa cgtgatttca agctgaaact acaaggtcag ctggggagga agggacctct | 1200 |
| gtcagtttca actgaggtgt ttgaggtggc accttctctt tacatggttg agttacagaa | 1260 |
| gaacagcggc gatacgttgg agtacaataa cttttataag aatctttcca agggtctcaa | 1320 |
| agacatcgtg tggaaagcag accctattcc tacaagtgag caaaagtaga aagcttccgc | 1380 |
| tacggcttta atatatgccc gtgctgtgaa gtgcccgagc tcat | 1424 |

<210> SEQ ID NO 5
<211> LENGTH: 2011
<212> TYPE: DNA
<213> ORGANISM: Physcomitrella patens

<400> SEQUENCE: 5

| | |
|---|---|
| atcccgggcg cgcacaattt cagttgggaa tcaagctgga aaagtttttt cctctagtgg | 60 |
| ctgagctggc caaggaactg gccattggac tcttcttaca aactagtcaa gtccgtattg | 120 |
| taggagccaa tgctgttgaa cccaaccagg acaagacaaa cgtgagtgca gattttgtgc | 180 |
| cgctagatac caaatttgat cacaccactg cccatcttct tgctacacgc ttgtggagtg | 240 |
| gtgaagttcc attgaacaag cactatttg gaacctacta tgttatttat ataatttacc | 300 |
| caggtcttcc tccctctcca cctccccagt tccctgggaa tatttcacct tcaggtcctg | 360 |
| tcaaccagct tccatctggg gtggatccaa ataaaacaaa tcataaactc agttcgggaa | 420 |
| tgattaccgt gattgctttg gcttcggtta tgggtgtatt gttatttatt gggattgtat | 480 |
| ggctcattct cctacgccgc agcctggatg agaaaacttc gccttcggtt gtcggtcctc | 540 |
| tacatgctta tttcaaccct aaacctgaag gtgtgcaact gatccaactg agaatgaatg | 600 |
| cttatttcaa ctctaaacct gaagggtcat tattatcagg aagtatggca agctctacaa | 660 |
| cgatttctta tggatctagc atggccaact acacatgcac tgctaagacg ttcactttag | 720 |
| cagaattaga aagagcaaca gataattta gacctgataa tgtagtcggc gaagggggct | 780 |
| ttggtcgagt ttaccaaggg gtacttgata gtggtattga agtggctgta aaggtgctga | 840 |
| caagggatga tcatgagggt ggtcgtgagt ttgttgcgga ggtagaaatg ttaagcagat | 900 |
| tgcaccatcg caaccttgcg aagctaattg gcatctgtac tgaggaaata cgatgtttgg | 960 |
| tttatgagct catcacgaac gggagcgtgg aatctcactt gcatggtcta gataaataca | 1020 |
| ctgctcctct caactgggat gcacgtgtta aaattgcatt aggagctgct cgtgggctgg | 1080 |
| catacctgca cgaagattct cagcctaggg ttattcatag agattttaaa ggaagcaaca | 1140 |
| ttctacttga ggacgattac actccaaaag tatctgattt tggtctagct aaatcggcaa | 1200 |
| ctgagggagg caaggagcat atttccactc gagtaatggg cacgtttgga tatgtggctc | 1260 |
| ctgaatacgc aatgacagga catttgcttg tgaagagtga cgtttatagt tatggagtgg | 1320 |
| tactgctcga gctcctctcg gggcgtaaac ccgtggatat gtctcaacca cctgacaag | 1380 |
| agaatctagt tacttgggca cgcccactcc ttacaagcaa ggatggacta gagcagcttg | 1440 |
| tggatcctta cctcaaagac aacttttccat ttgaccactt tgcgaaggta gctgcaatag | 1500 |
| cgtccatgtg tgtacaacct gaagtctctc atcgaccatt catgggcgag gtggtgcagg | 1560 |
| ccttgaaact tgtgtgcaat gaaacagaag ccaaagacgt cggacaggct aaaggaacag | 1620 |
| tttctcccac ttctgacttg gccgaaacac agaacacagg atttctgcgg gacgccacct | 1680 |

-continued

```
ttattagtgt tgattacgac tcggggccct tcgaaacctt ggatcttgaa cagcgaaagc    1740
ggaaacctct ttctgcttcg gctactatga gtggctctgg agggttctta cgacaacttt    1800
cggattcatt cagacgctac agtgtttctg cccctccaaa ggctgcttca ctgccaagaa    1860
cttcatggta tgcactgggt agttcaaaac ctgtaggaag catgagtgag ctagagcag     1920 ctagattctt agatcctcaa cgcaggagat tttacgggtt ttggccctaa ttcttccacg    1980
cctgttttga cctttgcggg cgttaacgca a                                   2011
```

<210> SEQ ID NO 6
<211> LENGTH: 1627
<212> TYPE: DNA
<213> ORGANISM: Physcomitrella patens

<400> SEQUENCE: 6

```
atcccgggcg gtttggacac gatgttccag tcctttatat atatgagaca cagctggaga     60
aaacagtgca agggaaaggt cttggaaagt ttttaatgca gttacttgag ttggttgcac    120
gaaagaacaa catgaaagca gtacttttag ctgtgcataa agaaacaca agggcgctaa     180 ccttttacaa tgaacgttta gggtataagt tggcaattag atcagcatca agtcaacaaa    240
gcacacaaac tgtcacagag atgaaatacg agattctttg taaaactttc gatgtggagt    300
acacagccgt tgtagaggaa cggcaagggg acatggattg tgaatcacgt gaagagagcg    360
ctggagaagc aagctgccag acagttgacg cagaggatca ggttttggat gactcacgtc    420
ctgatacaga atgtgagtca cggatcgaga gcgtgccaaa caccctacaa ggaatgaagt    480
acacacagta caatgtgagg ggcgacaagt ttgaagtcta cgacaagtat gtaatgattg    540
gtcccattgg tcatggagct tatgcgcatg tgtgtgcttt cacgaacagg agacaggggg   600
agaaagtggc cataaagaag attggaaacg catttcagaa caatactaca gcgaggcgca    660
cacttagaga gattttgttg ctccgccata ctgaacacga acatcattt cccatcagag    720 atatcattgt gcctgctaac attgaggact ttcatgatgc ctatatcgca aatgagctca    780
tggatacaga ccttcaccag atagtgaggt caacaaaaact tgacgaatac cattgccagt    840
tcctgcttta ccagctgttg agggggtctca aatacatcca ctctgccaat atattgcacc    900
gtgacctgaa gcccagtaat ctcctcatca attgcaacga ctgtctactc aagatttgtg    960
attttggctt ggctcgaaca tctgcagagg atgacttcct tacggagtat gttgttactc   1020
gaccatatcg agctccagag ctcttgcttg ggagccgaat gtacacagcg gctgttgata   1080
tgtggtcagt gggctgcatc ttcatggaga tgcttacagg acaacctttg tttccaatcc   1140
ggtcaaggca agggcatccc gtgaatcatt tgaaacccat cacggagctt ctaggaacac   1200
ccgatgcttc ggacctgtcg tttctgcaga atccagatgc tcggcaaaga atccaaatgg   1260
ctttgttagg tcaggaaagg aagcctttgt tttcgaggtt tcctcaaacg tctgcaatag   1320
cttgtgactt agcggagaag atgctgaggt ttaacccatc aacagaata actgcggaag   1380 aggccttggc ccatccttac ttggcagcgc ttcacgacct aagtgatgag ccaacgtgtc   1440
atcttatgtt cgacttcgat gcttaccttc ccagcctaac agttgagcat gtgaaaactc   1500
ttatctggag ggaagctaca cttatcaacg tccagtaatc gccataaaga tgtatcggac   1560
cagatgtcgc tgcaccaatt ggcaaagctt aagggttgag ggacttaaac gcggttagtt   1620
aacgcaa                                                             1627
```

<210> SEQ ID NO 7
<211> LENGTH: 441

```
<212> TYPE: PRT
<213> ORGANISM: Physcomitrella patens

<400> SEQUENCE: 7

Met Pro Thr Thr Asn Val Glu Arg Thr Arg Val Gly Lys Tyr Asp Leu
 1               5                  10                  15

Gly Lys Thr Leu Gly Glu Gly Thr Phe Ala Lys Val Lys Val Ala Lys
             20                  25                  30

His Ile Asp Thr Gly His Thr Val Ala Ile Lys Ile Leu Asp Lys Glu
         35                  40                  45

Lys Ile Leu Arg His Lys Met Val Glu Gln Ile Lys Arg Glu Ile Ser
 50                  55                  60

Thr Met Lys Leu Val Lys His Pro Tyr Val Val Gln Leu Leu Glu Val
 65                  70                  75                  80

Met Ala Ser Arg Thr Lys Ile Tyr Ile Val Leu Glu Tyr Val Thr Gly
                 85                  90                  95

Gly Glu Leu Phe Asn Lys Ile Ala Gln Gln Gly Arg Leu Ser Glu Asp
            100                 105                 110

Glu Ala Arg Lys Tyr Phe Gln Gln Leu Ile Asp Ala Val Asp Tyr Cys
        115                 120                 125

His Ser Arg Gln Val Tyr His Arg Asp Leu Lys Pro Glu Asn Leu Leu
    130                 135                 140

Leu Asp Ser Lys Gly Asn Leu Lys Ile Ser Asp Phe Gly Leu Ser Ala
145                 150                 155                 160

Leu Pro Gln Gln Phe Arg Glu Asp Gly Leu Leu His Thr Thr Cys Gly
                165                 170                 175

Thr Pro Asn Tyr Val Ala Pro Glu Val Ile Met Asp Lys Gly Tyr Ser
            180                 185                 190

Gly Ala Thr Ala Asp Leu Trp Ser Cys Gly Val Ile Leu Tyr Val Leu
        195                 200                 205

Met Ala Gly Tyr Leu Pro Phe Glu Glu Pro Thr Ile Met Ala Leu Tyr
    210                 215                 220

Lys Lys Ile Tyr Arg Ala Gln Phe Ser Trp Pro Pro Trp Phe Ser Ser
225                 230                 235                 240

Gly Ala Arg Lys Leu Ile Ser Lys Ile Leu Asp Pro Asn Pro Arg Thr
                245                 250                 255

Arg Ile Ser Ala Ser Gln Ile Tyr Lys Asn Asp Trp Phe Lys Lys Gly
            260                 265                 270

Tyr Thr Pro Ala Gln Phe Asp Arg Glu Val Asp Val Asn Leu Asp Asp
        275                 280                 285

Val Asn Ala Ile Phe Ser Cys Ser Gln Glu His Met Val Val Glu Arg
    290                 295                 300

Lys Glu Thr Lys Pro Val Ser Met Asn Ala Phe Glu Leu Ile Ser Met
305                 310                 315                 320

Ser Ser Gly Leu Asn Leu Ser Ser Leu Phe Glu Thr Lys Glu Ile Pro
                325                 330                 335

Glu Lys Glu Asp Thr Arg Phe Thr Ser Lys Ser Ala Lys Glu Ile
        340                 345                 350

Ile Ser Ser Ile Glu Glu Ala Ala Lys Pro Leu Gly Phe Asn Val Leu
    355                 360                 365

Lys Arg Asp Phe Lys Leu Lys Leu Gln Gly Gln Leu Gly Arg Lys Gly
    370                 375                 380

Pro Leu Ser Val Ser Thr Glu Val Phe Glu Val Ala Pro Ser Leu Tyr
385                 390                 395                 400
```

```
Met Val Glu Leu Gln Lys Asn Ser Gly Asp Thr Leu Glu Tyr Asn Asn
                405                 410                 415

Phe Tyr Lys Asn Leu Ser Lys Gly Leu Lys Asp Ile Val Trp Lys Ala
            420                 425                 430

Asp Pro Ile Pro Thr Ser Glu Gln Lys
        435                 440

<210> SEQ ID NO 8
<211> LENGTH: 516
<212> TYPE: PRT
<213> ORGANISM: Physcomitrella patens

<400> SEQUENCE: 8

Met Ile Thr Val Ile Ala Leu Ala Ser Val Met Gly Val Leu Leu Phe
  1               5                  10                  15

Ile Gly Ile Val Trp Leu Ile Leu Arg Arg Ser Leu Asp Glu Lys
                 20                  25                  30

Thr Ser Pro Ser Val Val Gly Pro Leu His Ala Tyr Phe Asn Pro Lys
             35                  40                  45

Pro Glu Gly Val Gln Leu Ile Gln Leu Arg Met Asn Ala Tyr Phe Asn
     50                  55                  60

Ser Lys Pro Glu Gly Ser Leu Leu Ser Gly Ser Met Ala Ser Ser Thr
 65                  70                  75                  80

Thr Ile Ser Tyr Gly Ser Ser Met Ala Asn Tyr Thr Cys Thr Ala Lys
                 85                  90                  95

Thr Phe Thr Leu Ala Glu Leu Glu Arg Ala Thr Asp Asn Phe Arg Pro
            100                 105                 110

Asp Asn Val Val Gly Glu Gly Gly Phe Gly Arg Val Tyr Gln Gly Val
            115                 120                 125

Leu Asp Ser Gly Ile Glu Val Ala Val Lys Val Leu Thr Arg Asp Asp
130                 135                 140

His Glu Gly Gly Arg Glu Phe Val Ala Glu Val Glu Met Leu Ser Arg
145                 150                 155                 160

Leu His His Arg Asn Leu Ala Lys Leu Ile Gly Ile Cys Thr Glu Glu
                165                 170                 175

Ile Arg Cys Leu Val Tyr Glu Leu Ile Thr Asn Gly Ser Val Glu Ser
            180                 185                 190

His Leu His Gly Leu Asp Lys Tyr Thr Ala Pro Leu Asn Trp Asp Ala
        195                 200                 205

Arg Val Lys Ile Ala Leu Gly Ala Ala Arg Gly Leu Ala Tyr Leu His
    210                 215                 220

Glu Asp Ser Gln Pro Arg Val Ile His Arg Asp Phe Lys Gly Ser Asn
225                 230                 235                 240

Ile Leu Leu Glu Asp Asp Tyr Thr Pro Lys Val Ser Asp Phe Gly Leu
                245                 250                 255

Ala Lys Ser Ala Thr Glu Gly Gly Lys Glu His Ile Ser Thr Arg Val
            260                 265                 270

Met Gly Thr Phe Gly Tyr Val Ala Pro Glu Tyr Ala Met Thr Gly His
        275                 280                 285

Leu Leu Val Lys Ser Asp Val Tyr Ser Tyr Gly Val Val Leu Leu Glu
    290                 295                 300

Leu Leu Ser Gly Arg Lys Pro Val Asp Met Ser Gln Pro Pro Gly Gln
305                 310                 315                 320

Glu Asn Leu Val Thr Trp Ala Arg Pro Leu Leu Thr Ser Lys Asp Gly
```

-continued

```
                325                 330                 335
Leu Glu Gln Leu Val Asp Pro Tyr Leu Lys Asp Asn Phe Pro Phe Asp
            340                 345                 350
His Phe Ala Lys Val Ala Ala Ile Ala Ser Met Cys Val Gln Pro Glu
            355                 360                 365
Val Ser His Arg Pro Phe Met Gly Glu Val Val Gln Ala Leu Lys Leu
            370                 375                 380
Val Cys Asn Glu Thr Glu Ala Lys Asp Val Gly Gln Ala Lys Gly Thr
385                 390                 395                 400
Val Ser Pro Thr Ser Asp Leu Ala Glu Thr Gln Asn Thr Gly Phe Leu
            405                 410                 415
Arg Asp Ala Thr Phe Ile Ser Val Asp Tyr Asp Ser Gly Pro Phe Glu
            420                 425                 430
Thr Leu Asp Leu Glu Gln Arg Lys Arg Lys Pro Leu Ser Ala Ser Ala
            435                 440                 445
Thr Met Ser Gly Ser Gly Gly Phe Leu Arg Gln Leu Ser Asp Ser Phe
            450                 455                 460
Arg Arg Tyr Ser Val Ser Ala Pro Pro Lys Ala Ala Ser Leu Pro Arg
465                 470                 475                 480
Thr Ser Trp Tyr Ala Leu Gly Ser Ser Lys Pro Val Gly Ser Met Ser
            485                 490                 495
Glu Ala Arg Ala Ala Arg Phe Leu Asp Pro Gln Arg Arg Phe Tyr
            500                 505                 510
Gly Phe Trp Pro
            515

<210> SEQ ID NO 9
<211> LENGTH: 480
<212> TYPE: PRT
<213> ORGANISM: Physcomitrella patens

<400> SEQUENCE: 9

Met Gln Leu Leu Glu Leu Val Ala Arg Lys Asn Asn Met Lys Ala Val
1               5                  10                  15
Leu Leu Ala Val His Lys Arg Asn Thr Arg Ala Leu Thr Phe Tyr Asn
            20                  25                  30
Glu Arg Leu Gly Tyr Lys Leu Ala Ile Arg Ser Ala Ser Ser Gln Gln
        35                  40                  45
Ser Thr Gln Thr Val Thr Glu Met Lys Tyr Glu Ile Leu Cys Lys Thr
    50                  55                  60
Phe Asp Val Glu Tyr Thr Ala Val Val Glu Glu Arg Gln Gly Asp Met
65                  70                  75                  80
Asp Cys Glu Ser Arg Glu Glu Ser Ala Gly Glu Ala Ser Cys Gln Thr
                85                  90                  95
Val Asp Ala Glu Asp Gln Val Leu Asp Asp Ser Arg Pro Asp Thr Glu
            100                 105                 110
Cys Glu Ser Arg Ile Glu Ser Val Pro Asn Thr Leu Gln Gly Met Lys
        115                 120                 125
Tyr Thr Gln Tyr Asn Val Arg Gly Asp Lys Phe Glu Val Tyr Asp Lys
    130                 135                 140
Tyr Val Met Ile Gly Pro Ile Gly His Gly Ala Tyr Gly Asp Val Cys
145                 150                 155                 160
Ala Phe Thr Asn Arg Glu Thr Gly Glu Lys Val Ala Ile Lys Lys Ile
                165                 170                 175
```

```
Gly Asn Ala Phe Gln Asn Asn Thr Thr Ala Arg Arg Thr Leu Arg Glu
            180                 185                 190

Ile Leu Leu Leu Arg His Thr Glu His Asp Asn Ile Ile Pro Ile Arg
        195                 200                 205

Asp Ile Ile Val Pro Ala Asn Ile Glu Asp Phe His Asp Ala Tyr Ile
    210                 215                 220

Ala Asn Glu Leu Met Asp Thr Asp Leu His Gln Ile Val Arg Ser Thr
225                 230                 235                 240

Lys Leu Asp Glu Tyr His Cys Gln Phe Leu Leu Tyr Gln Leu Leu Arg
                245                 250                 255

Gly Leu Lys Tyr Ile His Ser Ala Asn Ile Leu His Arg Asp Leu Lys
            260                 265                 270

Pro Ser Asn Leu Leu Ile Asn Cys Asn Asp Cys Leu Leu Lys Ile Cys
        275                 280                 285

Asp Phe Gly Leu Ala Arg Thr Ser Ala Glu Asp Phe Leu Thr Glu
    290                 295                 300

Tyr Val Val Thr Arg Pro Tyr Arg Ala Pro Glu Leu Leu Leu Gly Ser
305                 310                 315                 320

Arg Met Tyr Thr Ala Ala Val Asp Met Trp Ser Val Gly Cys Ile Phe
                325                 330                 335

Met Glu Met Leu Thr Gly Gln Pro Leu Phe Pro Ile Arg Ser Arg Gln
            340                 345                 350

Gly His Pro Val Asn His Leu Lys Pro Ile Thr Glu Leu Leu Gly Thr
        355                 360                 365

Pro Asp Ala Ser Asp Leu Ser Phe Leu Gln Asn Pro Asp Ala Arg Gln
    370                 375                 380

Arg Ile Gln Met Ala Leu Leu Gly Gln Glu Arg Lys Pro Leu Phe Ser
385                 390                 395                 400

Arg Phe Pro Gln Thr Ser Ala Ile Ala Cys Asp Leu Ala Glu Lys Met
                405                 410                 415

Leu Arg Phe Asn Pro Ser Asn Arg Ile Thr Ala Glu Glu Ala Leu Ala
            420                 425                 430

His Pro Tyr Leu Ala Ala Leu His Asp Leu Ser Asp Glu Pro Thr Cys
        435                 440                 445

His Leu Met Phe Asp Phe Asp Ala Tyr Leu Pro Ser Leu Thr Val Glu
    450                 455                 460

His Val Lys Thr Leu Ile Trp Arg Glu Ala Thr Leu Ile Asn Val Gln
465                 470                 475                 480

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 10
caggaaacag ctatgacc                                                 18

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 11
```

```
ctaaagggaa caaaagctg                                                 19

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 12
tgtaaaacga cggccagt                                                  18

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 13
ccgggctcct gacgagaacc aagga                                          25

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 14
atcccgggcg ttcaagcagg tgaatatgac aac                                 33

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 15
atgagctcgg gcacttcaca gcacgggcat at                                  32

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 16
gcccccttcg ccgactacat tatca                                          25

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 17
atcccgggcg cgcacaattt cagttgggaa tca                                 33

<210> SEQ ID NO 18
<211> LENGTH: 34
<212> TYPE: DNA
<213> ORGANISM: Artificial Sequence
```

```
<220> FEATURE:
<223> OTHER INFORMATION: Description of Artificial Sequence: Primer

<400> SEQUENCE: 18
gcgttaacgc ccgcaaaggt caaaacaggc gtgg                              34

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 19
gccgctgtgt acattcggct cccaag                                       26

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 20
atcccgggcg gtttggacac gatgttccag tcc                               33

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 21
gcgttaacta accgcgttta agtccctcaa c                                 31

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 22
ctagtaacat agatgacacc                                              20

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 23
atcccgggcg ttcaagcagg tgaatatgac aac                               33

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
gaatagatac gctgacacgc                                              20
```

```
<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 25
gcgttaacgc ccgcaaaggt caaaacaggc gtgg                          34

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 26
atcccgggcg cgcacaattt cagttgggaa tca                           33

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 27
atcccgggcg gtttggacac gatgttccag tcc                           33

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 28
gcgttaacta accgcgttta agtccctcaa c                             31
```

PROTEIN KINASE STRESS-RELATED PROTEINS AND METHODS OF USE IN PLANTS

CROSS-REFERENCE TO RELATED APPLICATIONS

This application claims the priority benefit of PCT/US00/34970 filed on Dec. 22, 2000 which relies upon the priority of U.S. Provisional Application Ser. No. 60/171,745 filed Dec. 22, 1999.

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Environmental stress due to salinity and drought are among the most serious factors limiting the productivity of agricultural crops. It is estimated that 35-45% of the 279 million hectares of land irrigation is presently affected by high salinity. This is exclusive of the regions classified as arid and desert lands. The consequence represents a significant economic and political factor and contributes to food shortages in many underdeveloped countries. In addition to salinity stress, crop yield losses due to drought in crops such as soybean, corn, rice and cotton also represent a significant economic factor. Moreover, drought is also responsible for food shortages in many countries worldwide. Developing crops tolerant to salt and drought is a strategy that has potential to alleviate some of these adverse situations.

Traditional plant breeding strategies to develop new lines of plants that exhibit tolerance to drought or salt tolerance are relatively slow and require specific tolerant lines for crossing with the desired commercial lines. Limited germplasm resources and incompatibility in crosses between distantly related plant species also represent a significant problem encountered in conventional breeding. In contrast, plant genetic transformation and availability of useful genes subjected to specific expression patterns allow one to generate stress tolerant plants using transgenic approaches.

Drought, cold as well as salt stresses have a common theme important for plant growth and that is water availability. Plants are exposed during their entire life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Since high salt content in some soils result in less available water for cell intake, its effect is similar to those observed under drought conditions. Additionally, under freezing temperatures, plant cells loose water as a result of ice formation that starts in the apoplast and withdraws water from the symplast. Commonly, a plant's molecular response mechanisms to each of these stress condition are common and protein kinases play an essential role in these molecular mechanisms.

Protein kinases represent a super family and the members of this family catalyze the reversible transfer of a phosphate group of ATP to serine, threonine and tyrosine amino acid side chains on target proteins. Protein kinases are primary elements in signaling processes in plants and have been reported to play crucial roles in perception and transduction of signals that allow a cell (and the plant) to respond to environmental stimuli. In particular, receptor protein kinases (RPKs) represent one group of protein kinases that activate a complex array of intracellular signaling pathways in response to the extracellular environment (Van der Gear et al., 1994 Annu. Rev. Cell Biol. 10:251-337). RPKs are single-pass transmembrane proteins that contain an amino-terminal signal sequence, extracellular domains unique to each receptor, and a cytoplasmic kinase domain. Ligand binding induces homo- or hetero-dimerization of RPKs, and the resultant close proximity of the cytoplasmic domains results in kinase activation by transphosphorylation. Although plants have many proteins similar to RPKs, no ligand has been identified for these receptor-like kinases (RLKs). The majority of plant RLKs that have been identified belong to the family of Serine/Threonine (Ser/Thr) kinases, and most have extracellular Leucine-rich repeats (Becraft, P W., 1998 Trends Plant Sci. 3:384-388).

Another type of protein kinase is the Ca+-dependent protein kinase (CDPK). This type of kinase has a calmodulin-like domain at the COOH terminus which allows response to Ca+ signals directly without calmodulin being present. Currently, CDPKs are the most prevalent Ser/Thr protein kinases found in higher plants. Although their physiological roles remain unclear, they are induced by cold, drought and abscisic acid (ABA) (Knight et al., 1991 Nature 352:524; Schroeder, J I and Thuleau, P., 1991 Plant Cell 3:555; Bush, D. S., 1995 Annu. Rev. Plant Phys. Plant Mol. Biol. 46:95; Urao, T. et al., 1994 Mol. Gen. Genet. 244:331).

Another type of signaling mechanism involves members of the conserved SNF1 Serine/Threonine protein kinase family. These kinases play essential roles in eukaryotic glucose and stress signaling (1). Plant SNF1-like kinases participate in the control of key metabolic enzymes, including HMGR, nitrate reductase, sucrose synthase, and sucrose phosphate synthase (SPS) (4). Genetic and biochemical data indicate that sugar-dependent regulation of SNF1 kinases involves several other sensory and signaling components in yeast, plants and animals.

Additionally, members of the Mitogen-activated protein kinase (MAPK) family have been implicated in the actions of numerous environmental stresses in animals, yeasts and plants. It has been demonstrated that both MAPK-like kinase activity and mRNA levels of the components of MAPK cascades increase in response to environmental stress and plant hormone signal transduction. MAP kinases are components of sequential kinase cascades, which are activated by phosphorylation of threonine and tyrosine residues by intermediate upstream MAP kinase kinases (MAPKKs). The MAPKKs are themselves activated by phosphorylation of serine and threonine residues by upstream kinases (MAPKKKs). A number of MAP Kinase genes have been reported in higher plants.

SUMMARY OF THE INVENTION

The present invention provides a transgenic plant transformed by a protein kinase stress-related protein (PKSRP) coding nucleic acid, wherein expression of the nucleic acid sequence in the plant results in increased tolerance to environmental stress as compared to a wild type variety of the plant. The invention provides that the PKSRP can be selected from any of the well known general classes of protein kinase proteins, including but not limited to: 1) Receptor Protein Kinases (RPK); 2) Receptor-Like Kinases (RLK); 3) Calcium Dependent Protein Kinases (CDPK); 4) SNF1 Serine/threonine Protein Kinases (SNF1); 5) Mitogen-activated Protein Kinases (MAPK); 6) intermediate upstream Mitogen-activated Protein Kinases (MAPKK); and upstream Mitogen-activated Protein Kinases (MAPKKK). The invention further provides specific examples of PKSRP, and PKSRP coding nucleic acids, such as 1) PK-1; 2) PK-2; and 3) MPK-1.

The invention provides in some embodiments that the PKSRP and coding nucleic acid are that found in members of the genus *Physcomitrella*. In another preferred embodiment, the nucleic acid and protein are from a *Physcomitrella patens* plant. The invention provides that the environmental stress can be salinity, drought, temperature, metal, chemical, pathogenic and oxidative stresses, or combinations thereof In preferred embodiments, the environmental stress can be salinity and drought, or a combination thereof.

The invention further provides a seed produced by a transgenic plant transformed by a PKSRP coding nucleic acid, wherein the plant is true breeding for increased tolerance to environmental stress as compared to a wild type variety of the plant. The invention further provides a seed produced by a transgenic plant expressing a PKSRP, wherein the plant is true breeding for increased tolerance to environmental stress as compared to a wild type variety of the plant.

The invention further provides an agricultural product produced by any of the transgenic plants described herein. The invention further provides an isolated PKSRP, wherein the PKSRP is as described below. The invention further provides an isolated PKSRP coding nucleic acid, wherein the PKSRP coding nucleic acid codes for a PKSRP as described below.

The invention further provides an isolated recombinant expression vector comprising a nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a PKSRP coding nucleic acid, wherein expression of the nucleic acid in the plant results in increased tolerance to environmental stress as compared to a wild type variety of the plant comprising: (a) transforming a plant cell with an expression vector comprising a PKSRP coding nucleic acid, and (b) generating from the plant cell a transgenic plant with an increased tolerance to environmental stress as compared to a wild type variety of the plant. In preferred embodiments, the PKSRP is as described below. In preferred embodiments, the PKSRP coding nucleic acid is as described below.

The present invention further provides a method of identifying a novel PKSRP, comprising (a) raising a specific antibody response to a PKSRP, or fragment thereof, as described above; (b) screening putative PKSRP material with the antibody, wherein specific binding of the antibody to the material indicates the presence of a potentially novel PKSRP; and (c) analyzing the bound material in comparison to known PKSRP to determine its novelty. Alternatively, hybridization with nucleic acid probes as described below can be used to identify novel PKSRP nucleic acids.

The present invention also provides methods of modifying stress tolerance of a plant comprising, modifying the expression of a PKSRP in the plant, wherein the PKSRP is as described below. The invention provides that this method can be performed such that the stress tolerance is either increased or decreased.

BRIEF DESCRIPTION OF THE DRAWINGS

FIG. 1(A-C) shows a nucleotide sequence of the partial PK-1 (SEQ ID NO:1); PK-2 (SEQ ID NO:2) and MPK-1 (SEQ ID NO: 3) from *Physcomitrella patens*

FIG. 2(A-C) shows a nucleotide sequence of the full-length PK-1 (SEQ ID NO:4), PK-2 (SEQ ID NO:5) and MPK-1 (SEQ ID NO:6) from *Physcomitrella patens*.

FIG. 3(A-C) shows a deduced amino acid sequence of PK-1 (SEQ ID NO:7), PK-2 (SEQ ID NO:8) and MPK-1 (SEQ ID NO:9).

FIG. 4 shows a diagram of the plant expression vector pGMSG containing the Super promoter driving the expression of SEQ ID NOs:4, 5 and 6. The components are: aacCI gentamycin resistance gene (Hajdukiewicz et al., 1994 Plant Molecular Biology 25:989-94), NOS promoter (Becker et al., 1992 Plant Molecular Biology 20:1195-7), g7T terminator (Becker et al., 1992), NOSpA terminator (Jefferson et al., 1987 EMBO J 6:3901-7). "Desired Gene" refers to the gene to be over-expressed in plants.

DETAILED DESCRIPTION OF THE INVENTION

Figure 5:
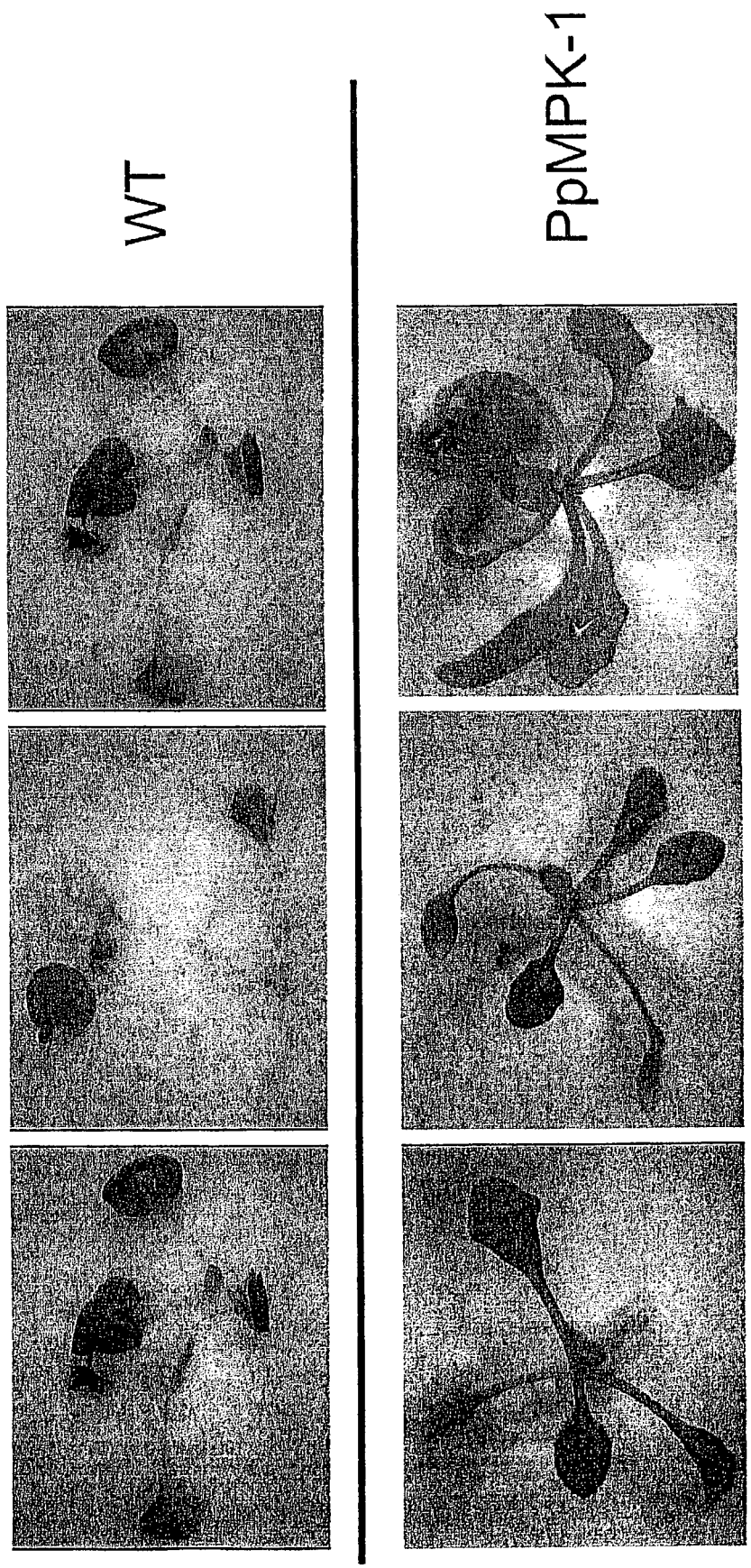
FIG. 5 shows the results of a drought stress test with over-expressing MPK-1 transgenic plants and wild-type *Arabidopsis* lines. The transgenic lines display a tolerant phenotype. Individual transformant lines are shown.
Figure 6:
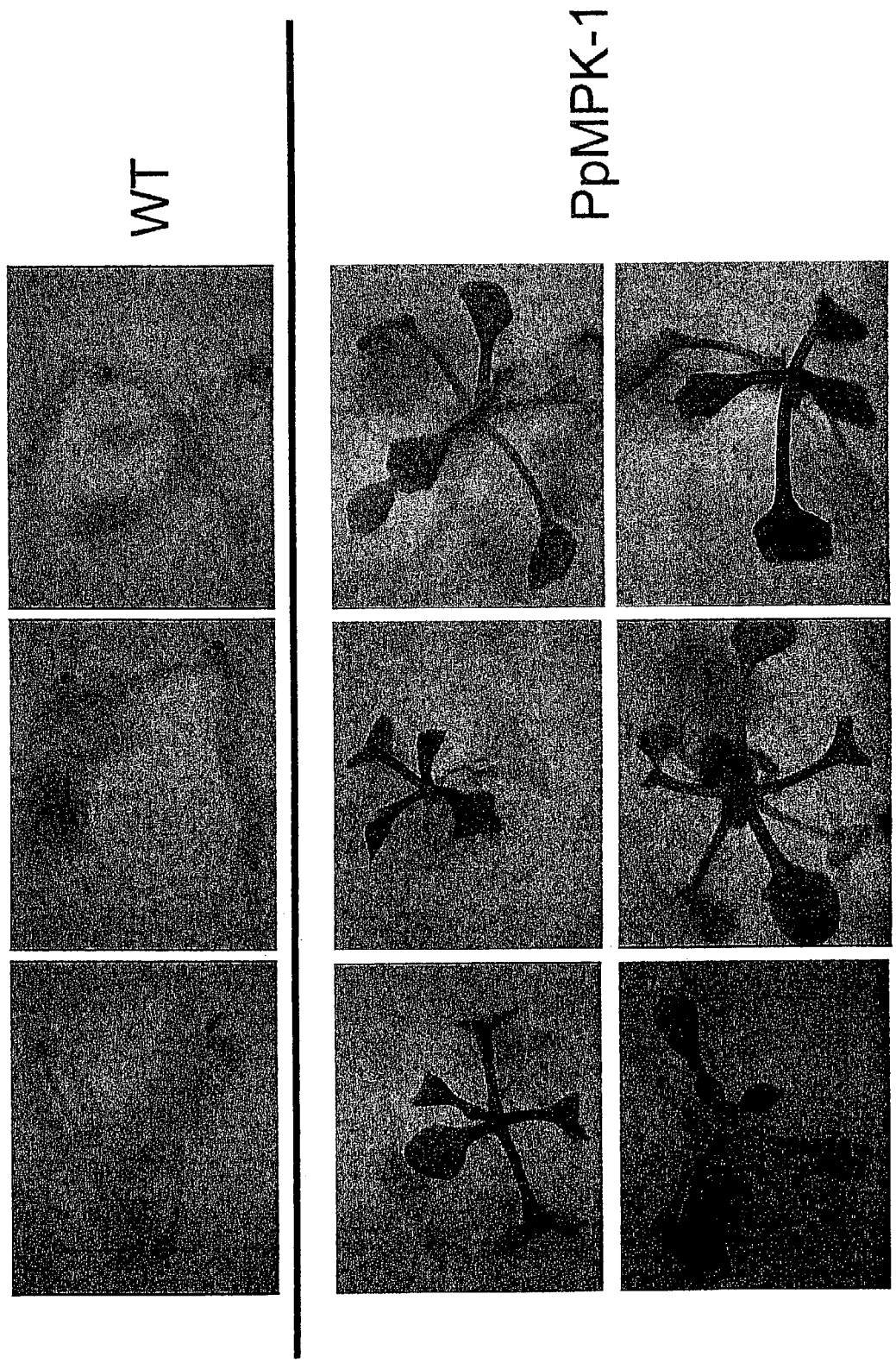
FIG. 6 shows the results of a salt stress test with over-expressing MPK-1 transgenic plants and wild-type *Arabidopsis* lines. The transgenic lines display a tolerant phenotype. Individual transformant lines are shown.
Figure 7:
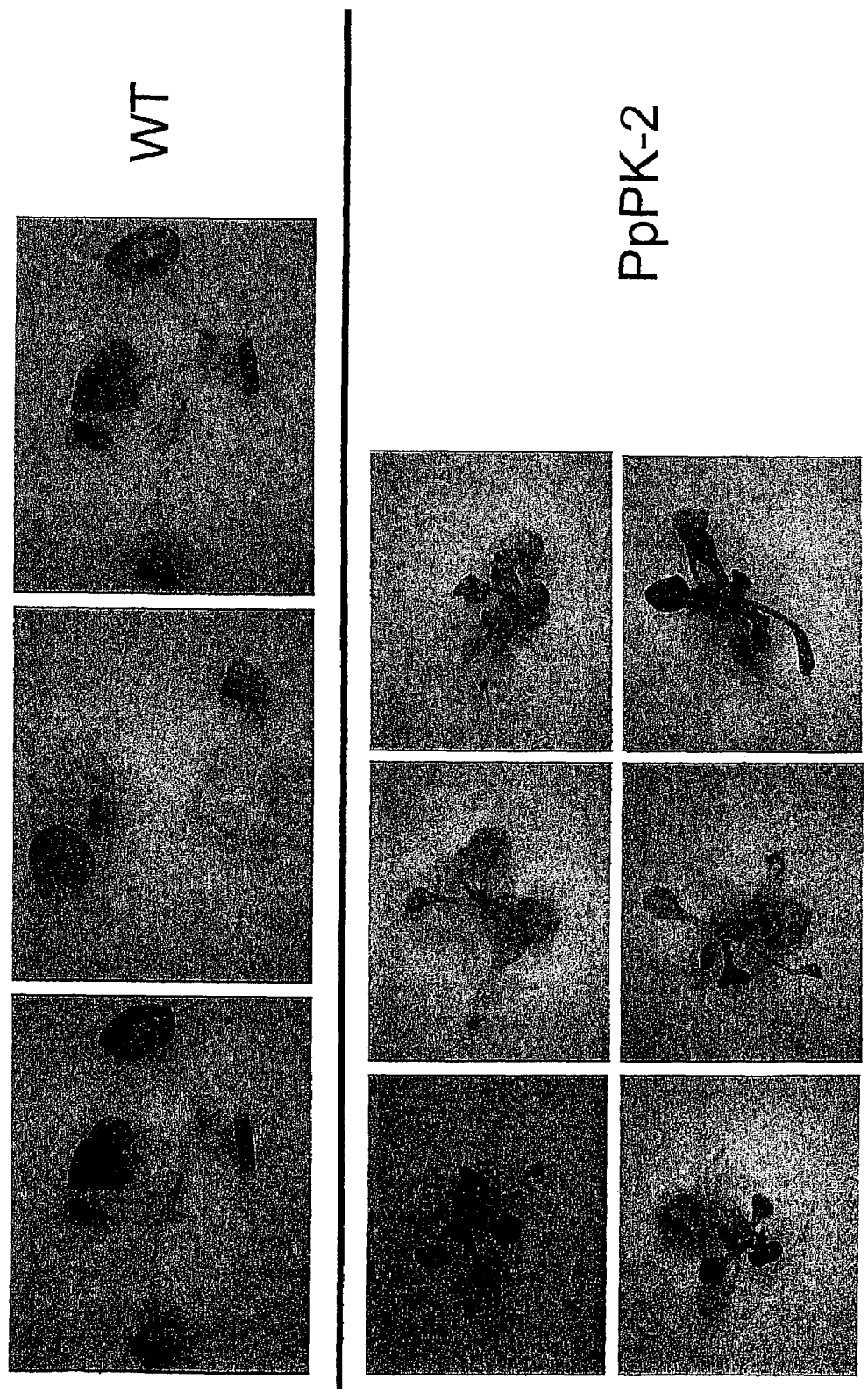
FIG. 7 shows the results of a drought stress test with over-expressing PK-2 transgenic plants and wild-type *Arabidopsis* lines. The transgenic lines display a tolerant phenotype. Individual transformant lines are shown.
Figure 8:
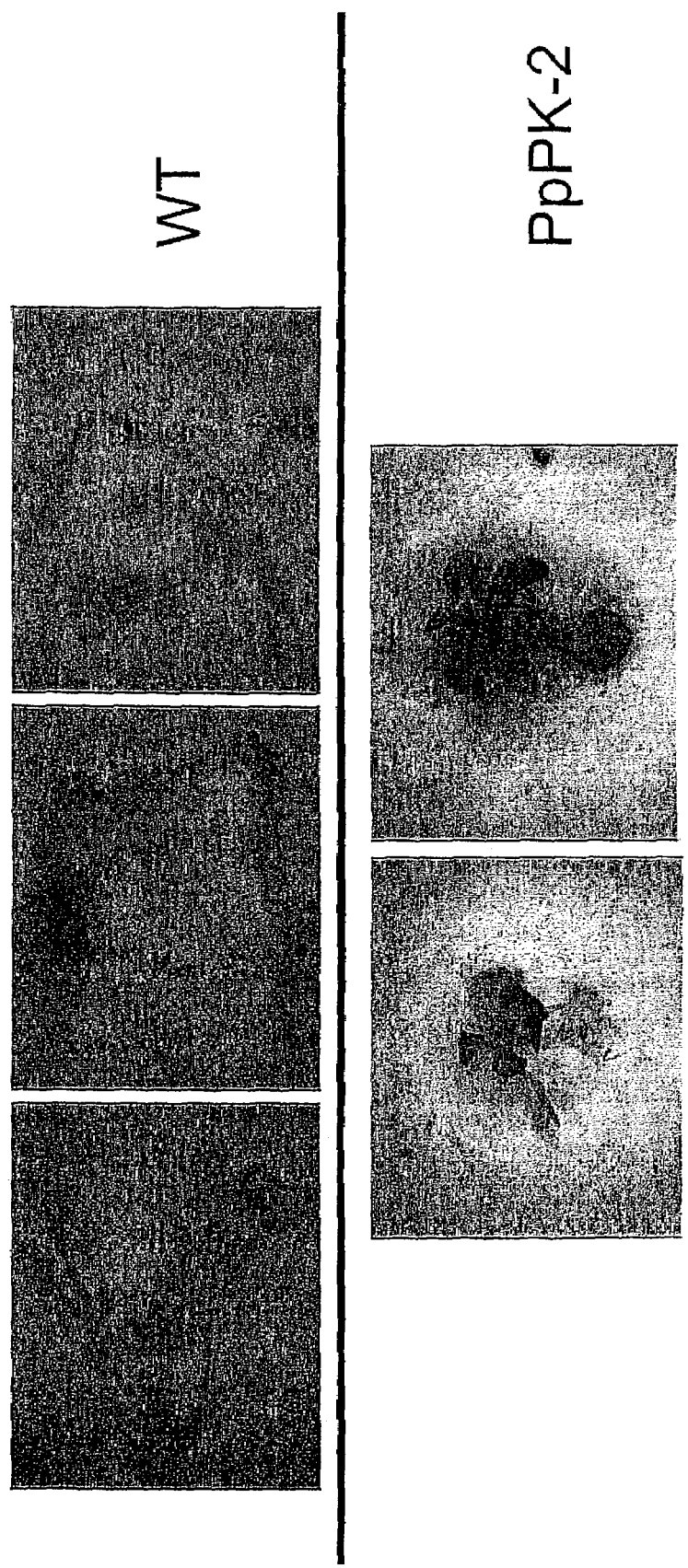
FIG. 8 shows the results of a Salt stress test with over-expressing PK-2 transgenic plants and wild-type *Arabidopsis* lines. The transgenic lines display a tolerant phenotype. Individual transformant lines are shown.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as "Protein Kinase Stress-related Proteins" (PKSRPs), in no way limits the functionality of those sequences.

The present invention provides a transgenic plant transformed by a PKSRP coding nucleic acid, wherein expression of the nucleic acid sequence in the plant results in increased tolerance to environmental stress as compared to a wild type variety of the plant. The invention further provides a seed produced by a transgenic plant transformed by a PKSRP coding nucleic acid, wherein the seed contains the PKSRP coding nucleic acid, and wherein the plant is true breeding for increased tolerance to environmental stress as compared to a wild type variety of the plant. The invention further provides a seed produced by a transgenic plant expressing a PKSRP, wherein the seed contains the PKSRP, and wherein the plant is true breeding for increased tolerance to environmental stress as compared to a wild type variety of the plant. The invention further provides an agricultural product produced by any of the above-or below-described transgenic plants. As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of a single DNA sequence introduced into a plant variety.

The invention further provides an isolated PKSRP. The invention provides that the PKSRP can be selected from one of the well known general classes of protein kinase proteins: 1) Receptor Protein Kinases (RPK); 2) Receptor-Like Kinases (RLK); 3) Calcium Dependent Protein Kinases (CDPK); 4) SNF1 Serine/threonine Protein Kinases (SNF1); 5) Mitogen-activated Protein Kinases (MAPK); 6) intermediate upstream Mitogen-activated Protein Kinases (MAPKK); and upstream Mitogen-activated Protein Kinases (MAPKKK). In further preferred embodiments, the PKSRP is selected from 1) Protein Kinase-1 (PK-1) as defined in SEQ ID NO:7; 2) Protein Kinase-1 (PK-2) as defined in SEQ ID NO:8; and 3) Mitogen-activated Protein Kinase-1 (MPK-1) as defined in SEQ ID NO:9; and homologues thereof. Homologues of the amino acid sequences are defined below.

The invention further provides an isolated PKSRP coding nucleic acid. In preferred embodiments the PKSRP coding nucleic acid is selected from 1) Protein Kinase-1 (PK-1) as defined in SEQ ID NO:4; 2) Protein Kinase-1 (PK-2) as defined in SEQ ID NO:5; and 3) Mitogen-activated Protein Kinase-1 (MPK-1) as defined in SEQ ID NO:6; and homologues thereof. Homologues of the nucleotide sequences are defined below. The present invention includes PKSRP coding nucleic acids that encode PKSRPs as described herein. In some embodiments, the invention provides that the PKSRP is selected from 1) Protein Kinase-1 (PK-1) as defined in SEQ ID NO:7; 2) Protein Kinase-1 (PK-2) as defined in SEQ ID NO:8; and 3) Mitogen-activated Protein Kinase-1 (MPK-1) as defined in SEQ ID NO:9. In one preferred embodiment, the nucleic acid and protein are isolated from the plant genus *Physcomitrella*. In another preferred embodiment, the nucleic acid and protein are from a *Physcomitrella patens* (*P. patens*) plant.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, and temperature, or combinations thereof, and in particular, can be high salinity, low water content and low temperature. It is also to be understood that as used in the specification and in the claims, "a" or "an" can mean one or more, depending upon the context in which it is used. Thus, for example, reference to "a cell" can mean that at least one cell can be utilized.

In accordance with the purposes of this invention, as embodied and broadly described herein, this invention, in one aspect, provides an isolated nucleic acid from a moss encoding a Stress-related Protein (SRP), or a portion thereof. In particular, the present invention provides nucleic acids encoding PKSRPs including the nucleic acid sequences shown in SEQ ID NO:4, SEQ ID NO:5 and SEQ ID NO:6. The present invention also provides amino acid sequences of PKSRPs including the amino acid sequences shown in SEQ ID NO:7, SEQ ID NO:8 and SEQ ID NO:9. As mentioned above, the present invention describes for the first time the predicted *P. patens* proteins Protein Kinase-1 (PK-1), Protein Kinase-1 (PK-2) and Mitogen-activated Protein Kinase-1 (MPK-1). The present invention also describes for the first time that the *P. patens* proteins Protein Kinase-1 (PK-1), Protein Kinase-1 (PK-2) and Mitogen-activated Protein Kinase-1 (MPK-1), are useful for increasing stress tolerance in plants.

A nucleic acid molecule of the present invention, e.g., a nucleic acid molecule having a nucleotide sequence of SEQ ID NO:4, SEQ ID NO:5 or SEQ ID NO:6, or a portion thereof, can be isolated using standard molecular biology techniques and the sequence information provided herein. For example, a *P. patens* PKSRP cDNA can be isolated from a *P. patens* library using all or portion of one of the sequences of SEQ ID NO:1, SEQ ID NO:2 and SEQ ID NO:3 as a hybridization probe and standard hybridization techniques (e.g., as described in Sambrook et al., 1989 *Molecular Cloning: A Laboratory Manual.* 2nd, ed., Cold Spring Harbor Laboratory, Cold Spring Harbor Laboratory Press, Cold Spring Harbor, N.Y.). Moreover, a nucleic acid molecule encompassing all or a portion of one of the sequences of SEQ ID NO:1, SEQ ID NO:2 and SEQ ID NO:3 can be isolated by the polymerase chain reaction using oligonucleotide primers designed based upon this sequence (e.g., a nucleic acid molecule encompassing all or a portion of one of the sequences of SEQ ID NO:1, SEQ ID NO:2 and SEQ ID NO:3 can be isolated by the polymerase chain reaction using oligonucleotide primers designed based upon this same sequence of SEQ ID NO:1, SEQ ID NO:2 or SEQ ID NO:3). For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney M L V reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:2 or SEQ ID NO:3. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a PKSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO: 4, SEQ ID NO:5 or SEQ ID NO:6. The sequences of SEQ ID NO:4, SEQ ID NO:5 or SEQ ID NO:6 correspond to the *Physcomitrella patens* PKSRP cDNAs of the invention. These cDNAs comprise sequences encoding PKSRPs (i.e., the "coding region", indicated in Table 1), as well as 5' untranslated sequences and 3' untranslated sequences. It is therefore to be understood that SEQ ID NO:4, SEQ ID NO:5 or SEQ ID NO:6 comprise both coding regions and 5' and 3' untranslated regions. Alternatively, the nucleic acid molecule can comprise only the coding region of any of the sequences in SEQ ID NO:4, SEQ ID NO:5 or SEQ ID NO:6 or can contain whole genomic fragments isolated from genomic DNA. A coding region of these sequences is indicated as "ORF position".

In another preferred embodiment, an isolated nucleic acid molecule of the invention comprises a nucleic acid molecule which is a complement of one of the nucleotide sequences shown in SEQ ID NO:4, SEQ ID NO:5 or SEQ ID NO:6, or a portion thereof. A nucleic acid molecule which is complementary to one of the nucleotide sequences shown in SEQ ID NO:4, SEQ ID NO:5 or SEQ ID NO:6 is one which is sufficiently complementary to one of the nucleotide sequences shown in SEQ ID NO:4, SEQ ID NO:5 or SEQ ID NO:6 such that it can hybridize to one of the nucleotide sequences shown in SEQ ID NO:4, SEQ ID NO:5 or SEQ ID NO:6, thereby forming a stable duplex.

In still another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown in SEQ ID NO:4, SEQ ID NO:5 or SEQ ID NO:6, or a portion thereof. In an additional preferred embodiment, an isolated nucleic acid molecule of the invention comprises a nucleotide sequence which hybridizes, e.g., hybridizes under stringent conditions, to one of the nucleotide sequences shown in SEQ ID NO:4, SEQ ID NO:5 or SEQ ID NO:6, or a portion thereof. These hybridization conditions include washing with a solution having a salt concentration of about 0.02 molar at pH 7 at about 60° C.

Moreover, the nucleic acid molecule of the invention can comprise only a portion of the coding region of one of the sequences in SEQ ID NO:4, SEQ ID NO:5 and SEQ ID NO:6, for example a fragment which can be used as a probe or primer or a fragment encoding a biologically active portion of a PKSRP. The nucleotide sequences determined from the cloning of the PKSRP genes from *P. patens* allows for the generation of probes and primers designed for use in identifying and/or cloning PKSRP homologues in other cell types and organisms, as well as PKSRP homologues from other mosses or related species. Therefore this invention also provides compounds comprising the nucleic acid molecules disclosed herein, or fragments thereof. These compounds include the nucleic acid molecules attached to a moiety. These moieties include, but are not limited to, detection moieties, hybridization moieties, purification moieties, delivery moieties, reaction moieties, binding moieties, and the like. The probe/primer typically comprises substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:4, SEQ ID NO:5 or SEQ ID NO:6, an anti-sense sequence of one of the sequences set forth in SEQ ID NO:4, SEQ ID NO:5 or SEQ ID NO:6, or naturally occurring mutants thereof. Primers based on a nucleotide sequence of SEQ ID NO:4, SEQ ID NO:5 or SEQ ID NO:6 can be used in PCR reactions to clone PKSRP homologues. Probes based on the PKSRP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an PKSRP, such as by measuring a level of a PKSRP-encoding nucleic acid in a sample of cells, e.g., detecting PKSRP mRNA levels or determining whether a genomic PKSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317-326.

To assess the presence or relative quantity of protein translated from this mRNA, standard techniques, such as a Western blot, may be employed (see, for example, Ausubel et al., 1988 Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or calorimetric label that may be readily detected. The presence and quantity of label observed indicates the presence and quantity of the desired mutant protein present in the cell.

In one embodiment, the nucleic acid molecule of the invention encodes a protein or portion thereof which includes an amino acid sequence which is sufficiently homologous to an amino acid sequence of SEQ ID NO:7, SEQ ID NO:8 or SEQ ID NO:9 such that the protein or portion thereof maintains the same or a similar function as the amino acid sequence to which it is compared. As used herein, the language "sufficiently homologous" refers to proteins or portions thereof which have amino acid sequences which include a minimum number of identical or equivalent (e.g., an amino acid residue which has a similar side chain as an amino acid residue in one of the ORFs of a sequence of SEQ ID NO:7, SEQ ID NO:8 or SEQ ID NO:9) amino acid residues to a PKSRP amino acid sequence such that the protein or portion thereof is able to participate in a stress tolerance response in a plant, or more particularly can participate in protein kinase signal transduction mechanisms involved in a stress tolerance response in a *Physcomitrella patens* plant. Examples of such activities are also described herein. Examples of PKSRP activities are set forth in Table 1.

In another embodiment, the protein is at least about 50-60%, preferably at least about 60-70%, and more preferably at least about 70-80%, 80-90%, 90-95%, and most preferably at least about 96%, 97%, 98%, 99% or more homologous to an entire amino acid sequence shown in SEQ ID NO:7; SEQ ID NO:8 or SEQ ID NO:9. In yet another embodiment, at least about 50-60%, preferably at least about 60-70%, and more preferably at least about 70-80%, 80-90%, 90-95%, and most preferably at least about 96%, 97%, 98%, 99% or more homologous to an entire amino acid sequence encoded by a nucleic acid sequence shown in SEQ ID NO:4, SEQ ID NO:5 or SEQ ID NO:6.

Portions of proteins encoded by the PKSRP nucleic acid molecules of the invention are preferably biologically active portions of one of the PKSRPs. As used herein, the term "biologically active portion of a PKSRP" is intended to include a portion, e.g., a domain/motif, of a PKSRP that participates in a stress tolerance response in a plant, or more particularly participates in the protein kinase signal transduction mechanisms involved in a stress tolerance response in a plant, or has an activity as set forth in Table 1. To determine whether a PKSRP or a biologically active portion thereof can participate in protein kinase signal transduction mechanisms involved in a stress tolerance response in a plant, a stress analysis of a plant expressing the PKSRP may be performed. Such analysis methods are well known to those skilled in the art, as detailed in Example 7.

Additional nucleic acid fragments encoding biologically active portions of a PKSRP can be prepared by isolating a portion of one of the sequences in SEQ ID NO:7, SEQ ID NO:8 or SEQ ID NO:9, expressing the encoded portion of the PKSRP or peptide (e.g., by recombinant expression in vitro) and assessing the activity of the encoded portion of the PKSRP or peptide.

The invention further encompasses nucleic acid molecules that differ from one of the nucleotide sequences shown in SEQ ID NO:4, SEQ ID NO:5 or SEQ ID NO:6 (and portions thereof) due to degeneracy of the genetic code and thus encode the same PKSRP as that encoded by the nucleotide sequences shown in SEQ ID NO:4, SEQ ID NO:5 or SEQ ID NO:6. In a further embodiment, the nucleic acid molecule of the invention encodes a full length *Physcomitrella patens* protein which is substantially homologous to an amino acid sequence of a polypeptide shown in SEQ ID NO:7, SEQ ID NO:8 or SEQ ID NO:9.

In addition to the *Physcomitrella patens* PKSRP nucleotide sequences shown in SEQ ID NO:4, SEQ ID NO:5 and SEQ ID NO:6, it will be appreciated by those skilled in the art that DNA sequence polymorphisms that lead to changes in the amino acid sequences of PKSRPs may exist within a population (e.g., the *Physcomitrella patens* population). Such genetic polymorphism in the PKSRP gene may exist among individuals within a population due to natural variation. As used herein, the terms "gene" and "recombinant gene" refer to nucleic acid molecules comprising an open reading frame encoding a PKSRP, preferably a *Physcomitrella patens* PKSRP. Such natural variations can typically result in 1-5% variance in the nucleotide sequence of the PKSRP gene. Any and all such nucleotide variations and resulting amino acid polymorphisms in a PKSRP that are the result of natural variation and that do not alter the functional activity of the PKSRPs are intended to be within the scope of the invention.

Nucleic acid molecules corresponding to natural variants and non-*Physcomitrella patens* homologues of the *Physcomitrella patens* PKSRP cDNA of the invention can be isolated based on their homology to *Physcomitrella patens* PKSRP nucleic acid disclosed herein using the *Physcomitrella patens* cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising a nucleotide sequence of SEQ ID NO:4, SEQ ID NO:5 or SEQ ID NO:6. In other embodiments, the nucleic acid is at least 30, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, 6.3.1-6.3.6, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC., 0.1% SDS at 50-65° C. Preferably, an isolated nucleic acid molecule of the invention that hybridizes under stringent conditions to a sequence of SEQ ID NO:4, SEQ ID NO:5 or SEQ ID NO:6 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *Physcomitrella patens* PKSRP.

In addition to naturally-occurring variants of the PKSRP sequence that may exist in the population, the skilled artisan will further appreciate that changes can be introduced by mutation into a nucleotide sequence of SEQ ID NO:4, SEQ ID NO:5 or SEQ ID NO:6, thereby leading to changes in the amino acid sequence of the encoded PKSRP, without altering the functional ability of the PKSRP. For example, nucleotide substitutions leading to amino acid substitutions at "non-essential" amino acid residues can be made in a sequence of SEQ ID NO:4, SEQ ID NO:5 or SEQ ID NO:6. A "non-essential" amino acid residue is a residue that can be altered from the wild-type sequence of one of the PKSRPs (SEQ ID NO:7, SEQ ID NO:8 and SEQ ID NO:9) without altering the activity of said PKSRP, whereas an "essential" amino acid residue is required for PKSRP activity. Other amino acid residues, however, (e.g., those that are not conserved or only semi-conserved in the domain having PKSRP activity) may not be essential for activity and thus are likely to be amenable to alteration without altering PKSRP activity.

Accordingly, another aspect of the invention pertains to nucleic acid molecules encoding PKSRPs that contain changes in amino acid residues that are not essential for PKSRP activity. Such PKSRPs differ in amino acid sequence from a sequence contained in SEQ ID NO:7, SEQ ID NO:8 or SEQ ID NO:9, yet retain at least one of the PKSRP activities described herein. In one embodiment, the isolated nucleic acid molecule comprises a nucleotide sequence encoding a protein, wherein the protein comprises an amino acid sequence at least about 50% homologous to an amino acid sequence of SEQ ID NO:7, SEQ ID NO:8 or SEQ ID NO:9 and is capable of participating in the a stress tolerance response in a plant, or more particularly participates in protein kinase signal transduction mechanisms involved in a stress tolerance response in a *Physcomitrella patens* plant, or has one or more activities set forth in Table 1. Preferably, the protein encoded by the nucleic acid molecule is at least about 50-60% homologous to one of the sequences of SEQ ID NO:7, SEQ ID NO:8 and SEQ ID NO:9, more preferably at least about 60-70% homologous to one of the sequences of SEQ ID NO:7, SEQ ID NO:8 and SEQ ID NO:9, even more preferably at least about 70-80%, 80-90%, 90-95% homologous to one of the sequences of SEQ ID NO:7, SEQ ID NO:8 and SEQ ID NO:9, and most preferably at least about 96%, 97%, 98%, or 99% homologous to one of the sequences of SEQ ID NO:7, SEQ ID NO:8 and SEQ ID NO:9.

To determine the percent homology of two amino acid sequences (e.g., one of the sequences of SEQ ID NO:7, SEQ ID NO:8 and SEQ ID NO:9 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences of SEQ ID NO:7, SEQ ID NO:8 and SEQ ID NO:9) is occupied by the same amino acid residue or nucleotide as the corresponding position in the other sequence (e.g., a mutant form of the sequence selected from the polypeptide of SEQ ID NO:7, SEQ ID NO:8 or SEQ ID NO:9), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100). Preferably, the length of sequence comparison is at least 15 amino acid residues, more preferably at least 25 amino acid residues, and most preferably at least 35 amino acid residues.

Alternatively, a determination of the percent homology between two sequences can be accomplished using a mathematical algorithm. A preferred, non-limiting example of a mathematical algorithm utilized for the comparison of two sequences is the algorithm of Karlin and Altschul (1990 Proc. Natl. Acad. Sci. USA 90:5873-5877). Such an algorithm is incorporated into the NBLAST and XBLAST programs of Altschul, et al. (1990 J. Mol. Biol. 215:403-410). BLAST nucleic acid searches can be performed with the NBLAST program, score=100, wordlength=12 to obtain nucleic acid sequences homologous to PKSRP nucleic acid molecules of the invention. BLAST protein searches can be performed with the XBLAST program, score=50, wordlength=3 to obtain amino acid sequences homologous to PKSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

be used to obtain amino acid sequences homologous to the PKSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

An isolated nucleic acid molecule encoding a PKSRP homologous to a protein sequence of SEQ ID NO:7, SEQ ID NO:8 or SEQ ID NO:9 can be created by introducing one or more nucleotide substitutions, additions or deletions into a nucleotide sequence of SEQ ID NO:4, SEQ ID NO:5 or SEQ ID NO:6 such that one or more amino acid substitutions, additions or deletions are introduced into the encoded protein. Mutations can be introduced into one of the sequences of SEQ ID NO:4, SEQ ID NO:5 and SEQ ID NO:6 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PKSRP is preferably replaced with another amino acid residue from the same side chain family. Alternatively, in another embodiment, mutations can be introduced randomly along all or part of a PKSRP coding sequence, such as by saturation mutagenesis, and the resultant mutants can be screened for a PKSRP activity described herein to identify mutants that retain PKSRP activity. Following mutagenesis of one of the sequences of SEQ ID NO:4, SEQ ID NO:5 and SEQ ID NO:6, the encoded protein can be expressed recombinantly and the activity of the protein can be determined by analyzing the stress tolerance of a plant expressing the protein as described in Example 7.

In addition to the nucleic acid molecules encoding PKSRPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PKSRP coding strand, or to only a portion thereof. In one embodiment, an antisense nucleic acid molecule is antisense to a "coding region" of the coding strand of a nucleotide sequence encoding a PKSRP. The term "coding region"

refers to the region of the nucleotide sequence comprising codons which are translated into amino acid residues (e.g., the entire coding region of , , , comprises nucleotides 1 to . . . ). In another embodiment, the antisense nucleic acid molecule is antisense to a "noncoding region" of the coding strand of a nucleotide sequence encoding PKSRP. The term "noncoding region" refers to 5' and 3' sequences that flank the coding region that are not translated into amino acids (i.e., also referred to as 5' and 3' untranslated regions).

Given the coding strand sequences encoding PKSRP disclosed herein (e.g., the sequences set forth in SEQ I) NO:4, SEQ ID NO:5 and SEQ ID NO:6), antisense nucleic acids of the invention can be designed according to the rules of Watson and Crick base pairing. The antisense nucleic acid molecule can be complementary to the entire coding region of PKSRP mRNA, but more preferably is an oligonucleotide which is antisense to only a portion of the coding or noncoding region of PKSRP mRNA. For example, the antisense oligonucleotide can be complementary to the region surrounding the translation start site of PKSRP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a PKSRP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoters are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625-6641). The antisense nucleic acid molecule can also comprise a 2'-o-methylribonucleotide (Inoue et al., 1987 Nucleic Acids Res. 15:6131-6148) or a chimeric RNA-DNA analogue (Inoue et al., 1987 FEBS Lett. 215: 327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988 Nature 334:585-591)) can be used to catalytically cleave PKSRP mRNA transcripts to thereby inhibit translation of PKSRP mRNA. A ribozyme having specificity for a PKSRP-encoding nucleic acid can be designed based upon the nucleotide sequence of a PKSRP cDNA disclosed herein (i.e., SEQ ID NO:4, SEQ ID NO:5 or SEQ ID NO:6) or on the basis of a heterologous sequence to be isolated according to methods taught in this invention. For example, a derivative of a *Tetrahymena* L-19 IVS RNA can be constructed in which the nucleotide sequence of the active site is complementary to the nucleotide sequence to be cleaved in an PKSRP-encoding mRNA. See, e.g., Cech et al. U.S. Pat. No. 4,987,071 and Cech et al. U.S. Pat. No. 5,116,742. Alternatively, PKSRP mRNA can be used to select a catalytic RNA having a specific ribonuclease activity from a pool of RNA molecules. See, e.g., Bartel, D. and Szostak, J. W., 1993 Science 261:1411-1418.

Alternatively, PKSRP gene expression can be inhibited by targeting nucleotide sequences complementary to the regulatory region of a PKSRP nucleotide sequence (e.g., a PKSRP promoter and/or enhancer) to form triple helical structures that prevent transcription of an PKSRP gene in target cells. See generally, Helene, C., 1991 Anticancer Drug Des. 6(6):569-84; Helene, C. et al., 1992 Ann. N.Y. Acad. Sci. 660:27-36; and Maher, L. J., 1992 Bioassays 14(12): 807-15.

The invention further provides an isolated recombinant expression vector comprising a nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PKSRPs, mutant forms of PKSRPs, fusion proteins, etc.).

The recombinant expression vectors of the invention can be designed for expression of PKSRPs in prokaryotic or eukaryotic cells. For example, PKSRP genes can be expressed in bacterial cells such as C. glutamicum, insect cells (using baculovirus expression vectors), yeast and other fungal cells (see Romanos, M. A. et al., 1992 Foreign gene expression in yeast: a review, Yeast 8:423-488; van den Hondel, C. A. M. J. J. et al., 1991 Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J., 1991 Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999 Marine Biotechnology 1(3):239-251), ciliates of the types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella, and Stylonychia, especially of the genus Stylonychia lemnae with vectors following a transformation method as described in WO 98/01572 and multicellular plant cells (see Schmidt, R. and Willmitzer, L., 1988 High efficiency Agrobacterium tumefaciens-mediated transformation of Arabidopsis thaliana leaf and cotyledon explants, Plant Cell Rep. 583-586); Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991 Annu. Rev. Plant Physiol. Plant Molec. Biol. 42:205-225 and references cited therein) or mammalian cells. Suitable host cells are discussed further in Goeddel, Gene Expression Technology: Methods in Enzymology 185, Academic Press: San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the PKSRP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant PKSRP unfused to GST can be recovered by cleavage of the fusion protein with thrombin.

Examples of suitable inducible non-fusion E. coli expression vectors include pTrc (Amann et al., 1988 Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111-2118). Such alteration of nucleic acid sequences of the invention can be carried out by standard DNA synthesis techniques.

In another embodiment, the PKSRP expression vector is a yeast expression vector. Examples of vectors for expression in yeast *S. cerevisiae* include pYepSec1 (Baldari, et al., 1987 Embo J. 6:229-234), pMFa (Kurjan and Herskowitz, 1982 Cell 30:933-943), pJRY88 (Schultz et al., 1987 Gene 54:113-123), and pYES2 (Invitrogen Corporation, San Diego, Calif.). Vectors and methods for the construction of vectors appropriate for use in other fungi, such as the filamentous fungi, includes those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge.

Alternatively, the PKSRPs of the invention can be expressed in insect cells using baculovirus expression vectors. Baculovirus vectors available, for expression of proteins in cultured insect cells (e.g., Sf 9 cells) include the pAc series (Smith et al., 1983 Mol. Cell Biol. 3:2156-2165) and the pVL series (Lucklow and Summers, 1989 Virology 170:31-39).

In yet another embodiment, a nucleic acid of the invent ion is expressed in mammalian cells using a mammalian expression vector. Examples of mammalian expression vectors include pCDM8 (Seed, B., 1987 Nature 329:840) and pMT2PC (Kaufman et al., 1987 EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268-277), lymphoid-specific promoters (Calame and Eaton, 1988 Adv. Immunol. 43:235-275), in particular promoters of T cell receptors (Winoto and Baltimore, 1989 EMBO J. 8:729-733) and immunoglobulins (Banerji et al., 1983 Cell 33:729-740; Queen and Baltimore, 1983 Cell 33:741-748), neuron-specific promoters (e.g., the neurofilament promoter; Byrne and Ruddle, 1989 *PNAS* 86:5473-5477), pancreas-specific promoters (Edlund et al., 1985 Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990 Science 249:374-379) and the fetoprotein promoter (Campes and Tilghman, 1989 Genes Dev. 3:537-546).

In another embodiment, the PKSRPs of the invention may be expressed in unicellular plant cells (such as algae) (see Falciatore et al., 1999 Marine Biotechnology 1(3):239-251 and references therein) and plant cells from higher plants (e.g., the spermatophytes, such as crop plants). Examples of plant expression vectors include those detailed in: Becker, D., Kemper, E., Schell, J. and Masterson, R., 1992 New plant binary vectors with selectable markers located proximal to the left border, *Plant Mol. Biol.* 20: 1195-1197; and Bevan, M. W., 1984 Binary Agrobacterium vectors for plant transformation, Nuel. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

A plant expression cassette preferably contains regulatory sequences capable of driving gene expression in plants cells and which are operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., 1987 Nucl. Acids Research 15:8693-8711).

Plant gene expression has to be operably linked to an appropriate promoter conferring gene expression in a timely, cell or tissue specific manner. Preferred are promoters driving constitutive expression (Benfey et al., 1989 EMBO J. 8:2195-2202) like those derived from plant viruses like the 35S CAMV (Franck et al., 1980 Cell 21:285-294), the 19S CaMV (see also U.S. Pat. No. 5,352,605 and WO8402913) or plant promoters like those from Rubisco small subunit described in U.S. Pat. No. 4,962,028.

Other preferred sequences for use in plant gene expression cassettes are targeting-sequences necessary to direct the gene product in its appropriate cell compartment (for review see Kermode, 1996 Crit. Rev. Plant Sci. 15(4):285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells. Plant gene expression can also be facilitated via an inducible promoter (for review see Gatz, 1997 Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (WO 95/19443), a tetracycline inducible promoter (Gatz et al., 1992 Plant J. 2:397-404) and an ethanol inducible promoter (WO 93/21334).

Also, suitable promoters responding to biotic or abiotic stress conditions are those such as the pathogen inducible PRP1-gene promoter (Ward et al., 1993 Plant. Mol. Biol. 22:361-366), the heat inducible hsp80-promoter from tomato (U.S. Pat. No. 5,187,267), cold inducible alpha-amylase promoter from potato (WO 96/12814) or the wound-inducible pinII-promoter (EP 375091). For other examples of drought, cold, and salt-inducible promoters, such as the RD29A promoter, see Yamaguchi-Shinozalei et al. (1993 Mol. Gen. Genet. 236:331-340).

Especially those promoters are preferred which confer gene expression in specific tissues and organs, such as guard cells and the root hair cells. Suitable promoters include the napin-gene promoter from rapeseed (U.S. Pat. No. 5,608,152), the USP-promoter from *Vicia faba* (Baeumlein et al., 1991 Mol Gen Genet. 225(3):459-67), the oleosin-promoter from Arabidopsis (WO9845461), the phaseolin-promoter from *Phaseolus vulgaris* (U.S. Pat. No. 5,504,200), the Bce4-promoter from Brassica (WO9113980) or the legumin B4 promoter (LeB4; Bacumlein et al., 1992 Plant Journal, 2(2):233-9) as well as promoters conferring seed specific expression in monocot plants like maize, barley, wheat, rye, rice, etc. Suitable promoters to note are the lpt2 or lpt1-gene promoter from barley (WO 95/15389 and WO 95/23230) or those desribed in WO 99/16890 (promoters from the barley hordein-gene, rice glutelin gene, rice oryzin gene, rice prolamin gene, wheat gliadin gene, wheat glutelin gene, maize zein gene, oat glutelin gene, Sorghum kasirin-gene and rye secalin gene).

Also especially suited are promoters that confer plastid-specific gene expression as plastids are the compartment where precursors and some end products of lipid biosynthesis are synthesized. Suitable promoters are the viral RNA-polymerase promoter described in WO 95/16783 and WO 97/06250 and the c1pP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to PKSRP mRNA. Regulatory sequences operatively linked to a nucleic acid molecule cloned in the antisense orientation can be chosen which direct the continuous expression of the antisense RNA molecule in a variety of cell types. For instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews-Trends in Genetics*, Vol. 1(1) 1986 and Mol et al., 1990 FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PKSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

Vector DNA can be introduced into prokaryotic or eukaryotic cells via conventional transformation or transfection techniques. As used herein, the terms "transformation", "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer and electroporation. Suitable methods for transforming or transfecting host cells including plant cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses and forage crops, these crops plants are also preferred target plants for a genetic engineering as one further embodiment of the present invention.

In particular, the invention provides a method of producing a transgenic plant with a PKSRP coding nucleic acid, wherein expression of the nucleic acid in the plant results in increased tolerance to environmental stress as compared to a wild type variety of the plant comprising: (a) transforming a plant cell with an expression vector comprising a PKSRP nucleic acid, and (b) generating from the plant cell a transgenic plant with a increased tolerance to environmental stress as compared to a wild type variety of the plant. In preferred embodiments, the PKSRP is as described above. In preferred embodiments, the PKSRP coding nucleic acid is as described above. The invention also provides a method of increasing expression of a gene of interest within a host cell as compared to a wild type variety of the host cell, wherein the gene of interest is transcribed in response to a PKSRP, comprising: (a) transforming the host cell with an expression vector comprising a PKSRP coding nucleic acid, and (b) expressing the PKSRP within the host cell, thereby increasing the expression of the gene transcribed in response to the PKSRP as compared to a wild type variety of the host cell. In preferred embodiments, the PKSRP is as described above. In preferred embodiments, the PKSRP coding nucleic acid is as described above.

For such plant transformation, binary vectors such as pBinAR can be used (Höfgen and Willmitzer, 1990 Plant Science 66:221-230). Construction of the binary vectors can be performed by ligation of the cDNA in sense or antisense orientation into the T-DNA. 5-prime to the cDNA a plant promoter activates transcription of the cDNA. A polyadenylation sequence is located 3-prime to the cDNA. Tissue-specific expression can be archived by using a tissue specific promoter. For example, seed-specific expression can be archived by cloning the napin or LeB4 or USP promoter 5-prime to the cDNA. Also, any other seed specific promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, Crit. Rev. Plant Sci., 1996 4 (15):285-423). The signal peptide is cloned 5-prime in frame to the cDNA to archive subcellular localization of the fusion protein. *Agrobacterium* mediated plant transformation can be performed using for example the GV3101(pMP90) (Koncz and Schell, 1986 Mol. Gen. Genet. 204:383-396) or LBA4404 (Clontech) *Agrobacterium tumefaciens* strain. Transformation can be performed by standard transformation techniques (Deblaere et al., 1994 Nucl. Acids. Res. 13:4777-4788). In one embodiment, promoters that are responsive to abiotic stresses can be used with, such as the *Arabidopsis* promoter RD29A, the nucleic acid sequences disclosed herein. One skilled in the art will recognize that the promoter used should be operatively linked to the nucleic acid such that the promoter causes transcription of the nucleic acid which results in the synthesis of a mRNA which encodes a polypeptide. Alternatively, the RNA can be an antisense RNA for use in affecting subsequent expression of the same or another gene or genes.

*Agrobacterium* mediated plant transformation can be performed using standard transformation and regeneration techniques (Gelvin, Stanton B. and Schilperoort, Robert A, Plant Molecular Biology Manual, 2nd Ed.—Dordrecht: Kluwer Academic Publ., 1995. —in Sect., Ringbuc Zentrale Signatur: BT11-P ISBN 0-7923-2731-4; Glick, Bernard R.; Thompson, John E., Methods in Plant Molecular Biology and Biotechnology, Boca Raton : CRC Press, 1993.—360 S.,ISBN 0-8493-5164-2). For example, rapeseed can be transformed via cotyledon or hypocotyl transformation (Moloney et al., 1989 Plant cell Report 8:238-242; De Block et al., 1989 Plant Physiol. 91:694-701). Use of antibiotica for Agrobacterium and plant selection depends on the binary vector and the Agrobacterium strain used for transformation. Rapeseed selection is normally performed using kanamycin as selectable plant marker. Agrobacterium mediated gene transfer to flax can be performed using, for example, a technique described by Mlynarova et al., 1994 Plant Cell Report 13: 282-285. Additionally, transformation of soybean can be performed using for example a technique described in EP 0424 047, U.S. Pat. No. 5,322,783 (Pioneer Hi-Bred International) or in EP 0397 687, U.S. Pat. No. 5,376,543, U.S. Pat. No. 5,169,770 (University Toledo).

Plant transformation using particle bombardment, Polyethylene Glycol mediated DNA uptake or via the Silicon Carbide Fiber technique is for example described by Freeling and Walbot "The maize handbook" Springer Verlag: New York (1993) ISBN 3-540-97826-7. A specific example of maize transformation is found in U.S. Pat. No. 5,990,387 and a specific example of wheat transformation can be found in WO 93/07256.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding an PKSRP or can be introduced on a separate vector. Cells stably transfected with the introduced nucleic acid molecule can be identified by, for example, drug selection (e.g., cells that have incorporated the selectable marker gene will survive, while the other cells die).

To create a homologous recombinant microorganism, a vector is prepared which contains at least a portion of a PKSRP gene into which a deletion, addition or substitution has been introduced to thereby alter, e.g., functionally disrupt, the PKSRP gene. Preferably, this PKSRP gene is a *Physcomitrella patens* PKSRP gene, but it can be a homologue from a related plant or even from a mammalian, yeast, or insect source. In a preferred embodiment, the vector is designed such that, upon homologous recombination, the endogenous PKSRP gene is functionally disrupted (i.e., no longer encodes a functional protein; also referred to as a knock-out vector). Alternatively, the vector can be designed such that, upon homologous recombination, the endogenous PKSRP gene is mutated or otherwise altered but still encodes functional protein (e.g., the upstream regulatory region can be altered to thereby alter the expression of the endogenous PKSRP). To create a point mutation via homologous recombination, DNA-RNA hybrids can be used in a technique known as chimeraplasty (Cole-Strauss et al., 1999 Nucleic Acids Research 27(5):1323-1330 and Kmiec, 1999 Gene therapy American Scientist. 87(3):240-247). Homologous recombination procedures in *Physcomitrella patens* are also well known in the art and are contemplated for use herein.

Whereas in the homologous recombination vector, the altered portion of the PKSRP gene is flanked at its 5' and 3' ends by additional nucleic acid molecule of the PKSRP gene to allow for homologous recombination to occur between the exogenous PKSRP gene carried by the vector and an endogenous PKSRP gene in a microorganism or plant. The additional flanking PKSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8):4368-4373 for cDNA based recombination in *Physcomitrella patens*). The vector is introduced into a microorganism or plant cell (e.g., via polyethylene glycol mediated DNA) and cells in which the introduced PKSRP gene has homologously recombined with the endogenous PKSRP gene are selected, using art-known techniques.

In another embodiment, recombinant microorganisms can be produced which contain selected systems which allow for regulated expression of the introduced gene. For example, inclusion of a PKSRP gene on a vector placing it under control of the lac operon permits expression of the PKSRP gene only in the presence of IPTG. Such regulatory systems are well known in the art.

A host cell of the invention, such as a prokaryotic or eukaryotic host cell in culture, can be used to produce (i.e., express) a PKSRP. An alternate method can be applied in addition in plants by the direct transfer of DNA into developing flowers via electroporation or Agrobacterium medium gene transfer. Accordingly, the invention further provides methods for producing PKSRPs using the host cells of the invention. In one embodiment, the method comprises culturing the host cell of invention (into which a recombinant expression vector encoding a PKSRP has been introduced, or into which genome has been introduced a gene encoding a wild-type or altered PKSRP) in a suitable medium until PKSRP is produced. In another embodiment, the method further comprises isolating PKSRPs from the medium or the host cell.

Another aspect of the invention pertains to isolated PKSRPs, and biologically active portions thereof. An "isolated" or "purified" protein or biologically active portion thereof is free of some of the cellular material when produced by recombinant DNA techniques, or chemical precursors or other chemicals when chemically synthesized. The language "substantially free of cellular material" includes preparations of PKSRP in which the protein is separated from some of the cellular components of the cells in which it is naturally or recombinantly produced. In one embodiment, the language "substantially free of cellular material" includes preparations of PKSRP having less than about 30% (by dry weight) of non-PKSRP (also referred to herein as a "contaminating protein"), more preferably less than about 20% of non-PKSRP, still more preferably less than about 10% of non-PKSRP, and most preferably less than about 5% non-PKSRP. When the PKSRP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of PKSRP in which the protein is separated from chemical precursors or other chemicals that are involved in the synthesis of the protein. In one embodiment, the language "substantially free of chemical precursors or other chemicals" includes preparations of PKSRP having less than about 30% (by dry weight) of chemical precursors or non-PKSRP chemicals, more preferably less than about 20% chemical precursors or non-PKSRP chemicals, still more preferably less than about 10% chemical precursors or non-PKSRP chemicals, and most preferably less than about 5% chemical precursors or non-PKSRP chemicals. In preferred embodiments, isolated proteins or biologically active portions thereof lack contaminating proteins from the same organism from which the PKSRP is derived. Typically, such proteins are produced by recombinant expression of, for example, a *Physcomitrella patens* PKSRP in plants other than *Physcomitrella patens* or microorganisms such as *C. glutamicum*, ciliates, algae or fungi.

An isolated PKSRP or a portion thereof of the invention can participate in a stress tolerance response in a plant, or more particularly can participate in the protein kinase signal transduction mechanisms involved in a stress tolerance response in a *Physcomitrella patens* plant, or has one or more of the activities set forth in Table 1. In preferred embodiments, the protein or portion thereof comprises an amino acid sequence which is sufficiently homologous to an amino acid sequence encoded by a nucleic acid of SEQ ID NO:4, SEQ ID NO:5 or SEQ ID NO:6 such that the protein or portion thereof maintains the ability to participate in the metabolism of compounds necessary for the construction of cellular membranes in *Physcomitrella patens*, or in the transport of molecules across these membranes. The portion of the protein is preferably a biologically active portion as described herein. In another preferred embodiment, a PKSRP of the invention has an amino acid sequence of SEQ ID NO:7, SEQ ID NO:8 or SEQ ID NO:9. In yet another preferred embodiment, the PKSRP has an amino acid sequence which is encoded by a nucleotide sequence which hybridizes, e.g., hybridizes under stringent conditions, to a nucleotide sequence of SEQ ID NO:4, SEQ ID NO:5 or SEQ ID NO:6. In still another preferred embodiment, the PKSRP has an amino acid sequence which is at least about 50-60%, preferably at least about 60-70%, more preferably at least about 70-80%, 80-90%, 90-95%, and even more preferably at least about 96%, 97%, 98%, 99% or more homologous to one of the amino acid sequences of SEQ ID NO:7, SEQ ID NO:8 and SEQ ID NO:9. The preferred PKSRPs of the present invention also preferably possess at least one of the PKSRP activities described herein. For example, a preferred PKSRP of the present invention includes an amino acid sequence encoded by a nucleotide sequence which hybridizes, e.g., hybridizes under stringent conditions, to a nucleotide sequence of SEQ ID NO:4, SEQ ID NO:5 or SEQ ID NO:6, and which can participate can participate in a stress tolerance response in a plant, or more particularly can participate in the transcription of a protein involved in a stress tolerance response in a *Physcomitrella patens* plant, or which has one or more of the activities set forth in Table 1.

In other embodiments, the PKSRP is substantially homologous to an amino acid sequence of SEQ ID NO:7, SEQ ID NO:8 or SEQ ID NO:9 and retains the functional activity of the protein of one of the sequences of SEQ ID NO:7, SEQ ID NO:8 and SEQ ID NO:9, yet differs in amino acid sequence due to natural variation or mutagenesis, as described in detail above. Accordingly, in another embodiment, the PKSRP is a protein which comprises an amino acid sequence which is at least about 50-60%, preferably at least about 60-70%, and more preferably at least about 70-80, 80-90, 90-95%, and most preferably at least about 96%, 97%, 98%, 99% or more homologous to an entire amino acid sequence of SEQ ID NO:7, SEQ ID NO:8 or SEQ ID NO:9 and which has at least one of the PKSRP activities described herein. In another embodiment, the invention pertains to a full *Physcomitrella patens* protein which is substantially homologous to an entire amino acid sequence encoded by a nucleic acid of SEQ ID NO:4, SEQ ID NO:5 or SEQ ID NO:6.

Biologically active portions of an PKSRP include peptides comprising amino acid sequences derived from the amino acid sequence of an PKSRP, e.g., an amino acid sequence of SEQ ID NO:7, SEQ ID NO:8 or SEQ ID NO:9 or the amino acid sequence of a protein homologous to an PKSRP, which include fewer amino acids than a full length PKSRP or the full length protein which is homologous to an PKSRP, and exhibit at least one activity of an PKSRP. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of a PKSRP. Moreover, other biologically active portions, in which other regions of the protein are deleted, can be prepared by recombinant techniques and evaluated for one or more of the activities described herein. Preferably, the biologically active portions of a PKSRP include one or more selected domains/motifs or portions thereof having biological activity.

PKSRPs are preferably produced by recombinant DNA techniques. For example, a nucleic acid molecule encoding the protein is cloned into an expression vector (as described above), the expression vector is introduced into a host cell (as described above) and the PKSRP is expressed in the host cell. The PKSRP can then be isolated from the cells by an appropriate purification scheme using standard protein purification techniques. Alternative to recombinant expression, a PKSRP, polypeptide, or peptide can be synthesized chemically using standard peptide synthesis techniques. Moreover, native PKSRP can be isolated from cells (e.g., *Physcomi-*

*trella patens*), for example using an anti-PKSRP antibody, which can be produced by standard techniques utilizing a PKSRP or fragment thereof of this invention.

The invention also provides PKSRP chimeric or fusion proteins. As used herein, a PKSRP "chimeric protein" or "fusion protein" comprises a PKSRP polypeptide operatively linked to a non-PKSRP polypeptide. An "PKSRP polypeptide" refers to a polypeptide having an amino acid sequence corresponding to a PKSRP, whereas a "non-PKSRP polypeptide" refers to a polypeptide having an amino acid sequence corresponding to a protein which is not substantially homologous to the PKSRP, e.g., a protein which is different from the PKSRP and which is derived from the same or a different organism. Within the fusion protein, the term "operatively linked" is intended to indicate that the PKSRP polypeptide and the non-PKSRP polypeptide are fused to each other so that both sequences fulfill the proposed function attributed to the sequence used. The non-PKSRP polypeptide can be fused to the N-terminus or C-terminus of the PKSRP polypeptide. For example, in one embodiment, the fusion protein is a GST-PKSRP fusion protein in which the PKSRP sequences are fused to the C-terminus of the GST sequences. Such fusion proteins can facilitate the purification of recombinant PKSRPs. In another embodiment, the fusion protein is a PKSRP containing a heterologous signal sequence at its N-terminus. In certain host cells (e.g., mammalian host cells), expression and/or secretion of a PKSRP can be increased through use of a heterologous signal sequence.

Preferably, a PKSRP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, *Current Protocols in Molecular Biology*, Eds. Ausubel et al. John Wiley & Sons: 1992). Moreover, many expression vectors are commercially available that already encode a fusion moiety (e.g., a GST polypeptide). A PKSRP-encoding nucleic acid can be cloned into such an expression vector such that the fusion moiety is linked in-frame to the PKSRP.

Homologues of the PKSRP can be generated by mutagenesis, e.g., discrete point mutation or truncation of the PKSRP. As used herein, the term "homologue" refers to a variant form of the PKSRP which acts as an agonist or antagonist of the activity of the PKSRP. An agonist of the PKSRP can retain substantially the same, or a subset, of the biological activities of the PKSRP. An antagonist of the PKSRP can inhibit one or more of the activities of the naturally occurring form of the PKSRP, by, for example, competitively binding to a downstream or upstream member of the cell membrane component metabolic cascade which includes the PKSRP, or by binding to an PKSRP which mediates transport of compounds across such membranes, thereby preventing translocation from taking place.

In an alternative embodiment, homologues of the PKSRP can be identified by screening combinatorial libraries of mutants, e.g., truncation mutants, of the PKSRP for PKSRP agonist or antagonist activity. In one embodiment, a variegated library of PKSRP variants is generated by combinatorial mutagenesis at the nucleic acid level and is encoded by a variegated gene library. A variegated library of PKSRP variants can be produced by, for example, enzymatically ligating a mixture of synthetic oligonucleotides into gene sequences such that a degenerate set of potential PKSRP sequences is expressible as individual polypeptides, or alternatively, as a set of larger fusion proteins (e.g., for phage display) containing the set of PKSRP sequences therein. There are a variety of methods which can be used to produce libraries of potential PKSRP homologues from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential PKSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477.

In addition, libraries of fragments of the PKSRP coding can be used to generate a variegated population of PKSRP fragments for screening and subsequent selection of homologues of a PKSRP. In one embodiment, a library of coding sequence fragments can be generated by treating a double stranded PCR fragment of a PKSRP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PKSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PKSRP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PKSRP homologues (Arkin and Yourvan, 1992 PNAS 89:7811-7815; Delgrave et al., 1993 Protein Engineering 6(3):327-331). In another embodiment, cell based assays can be exploited to analyze a variegated PKSRP library, using methods well known in the art. The present invention further provides a method of identifying a novel PKSRP, comprising (a) raising a specific antibody response to a PKSRP, or fragment thereof, as described above; (b) screening putative PKSRP material with the antibody, wherein specific binding of the antibody to the material indicates the presence of a potentially novel PKSRP; and (c) analyzing the bound material in comparison to known PKSRP to determine its novelty.

The nucleic acid molecules, proteins, protein homologues, fusion proteins, primers, vectors, and host cells described herein can be used in one or more of the following methods: identification of *Physcomitrella patens* and related organisms; mapping of genomes of organisms related to *Physcomitrella patens*; identification and localization of *Physcomitrella patens* sequences of interest; evolutionary studies; determination of PKSRP regions required for function; modulation of an PKSRP activity; modulation of the metabolism of one or more cell functions; modulation of the transmembrane transport of one or more compounds; and modulation of stress resistance.

The moss *Physcomitrella patens* represents one member of the mosses. It is related to other mosses such as *Ceratodon purpureus* which is capable of growth in the absence of light. Mosses like Ceratodon and Physcomitrella share a high degree of homology on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The PKSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a PKSRP coding nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and forage crops, for example. In particular, the present invention describes using the expression of PK-1 (SEQ ID NO:7), PK-2 (SEQ ID NO:8) and MPK-1 (SEQ ID NO:9) to engineer drought-tolerant plants. This strategy has herein been demonstrated for *Arabidopsis thaliana*, Rapeseed/Canola, soybeans, corn and wheat but its application is not restricted to these plants. Accordingly, the invention provides a transgenic plant containing a PKSRP selected from 1) PK-1; 2) PK-2; 3) PK-3 as defined above, including homologues, wherein the environmental stress is drought. This invention also describes the principle of using overexpression of PK-2 (SEQ ID NO:8) and MPK-1 (SEQ ID NO:9) to engineer salt-tolerant plants. Again, this strategy has herein been demonstrated for *Arabidopsis thaliana*, Rapeseed/Canola, soybeans, corn and wheat but its application is not restricted to these plants. Accordingly, the invention provides a transgenic plant containing the PKSRP selected from 1) PK-2 and 2) PK-3 as defined above, including homologues, wherein the environmental stress is salinity.

The present invention also provides methods of modifying stress tolerance of a plant comprising, modifying the expression of a PKSRP in the plant. The invention provides that this method can be performed such that the stress tolerance is either increased or decreased.

Furthermore, this method can be used wherein the plant is either transgenic or not transgenic. In cases when the plant is transgenic, the plant can be transformed with a vector containing any of the above described PKSRP coding nucleic acids, or the plant can be transformed with a promoter that directs expression of native PKSRP in the plant, for example. The invention provides that such a promoter can be tissue specific. Furthermore, such a promoter can be developmentally regulated. Alternatively, non-transgenic plants can have native PKSRP expression modified by inducing a native promoter. Furthermore, the invention provides that PKSRP expression can be modified by administration of an anti-sense molecule that inhibits expression of PKSRP.

The expression of PK-1 (SEQ ID NO:7), PK-2 (SEQ ID NO:8) and MPK-1 (SEQ ID NO:9) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657). The later case involves identification of the PK-1 (SEQ ID NO:7), PK-2 (SEQ ID NO:8) and MPK-1 (SEQ ID NO:9) homologues in the target plant as well as from its promoter. Zinc-finger-containing recombinant transcription factors are engineered to specifically interact with the PK-1 (SEQ ID NO:7), PK-2 (SEQ ID NO:8) and MPK-1 (SEQ ID NO:9) homologue and transcription of the corresponding gene is activated.

As shown herein and described more fully below, expression of the PKSRPs (PK-1 (SEQ ID NO:7), PK-2 (SEQ ID NO:8) and MPK-1 (SEQ ID NO:9)) in *Arabidopsis thaliana* confers a high degree of drought tolerance to the plant. Additionally, several PKSRPs confer tolerance to high salt concentrations (PK-2 (SEQ ID NO:8) and MPK-1 (SEQ ID NO:9)) to this plant.

In addition to introducing the PKSRP nucleic acid sequences into transgenic plants, these sequences can also be used to identify an organism as being *Physcomitrella patens* or a close relative thereof. Also, they may be used to identify the presence of *Physcomitrella patens* or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene which is unique to this organism, one can ascertain whether this organism is present.

Further, the nucleic acid and protein molecules of the invention may serve as markers for specific regions of the genome. This has utility not only in the mapping of the genome, but also in functional studies of *Physcomitrella patens* proteins. For example, to identify the region of the genome to which a particular *Physcomitrella patens* DNA-binding protein binds, the *Physcomitrella patens* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *Physcomitrella patens*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses.

The PKSRP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the PKSRP nucleic acid molecules of the invention may result in the production of PKSRPs having functional differences from the wild-type PKSRPs. These proteins may be improved in efficiency or activity, may be present in greater numbers in the cell than is usual, or may be decreased in efficiency or activity. There are a number of mechanisms by which the alteration of a PKSRP of the invention may directly affect stress response and/or stress tolerance. In the case of plants expressing PKSRPs, increased transport can lead to improved salt and/or solute partitioning within the plant tissue and organs. By either increasing the number or the activity of transporter molecules which export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived therefrom can then be assayed for fail or alteration of their tolerance to drought, salt, and temperature stress.

The engineering of one or more PKSRP genes of the invention may also result in PKSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226-235). While these products are typically excreted, cells can be genetically altered to transport more products than is typical for a wild-type cell. By optimizing the activity of one or more PKSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells. (Girke, T., 1998 The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation include U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246-252.

The aforementioned mutagenesis strategies for PKSRPs to result in increased stress resistance are not meant to be limiting; variations on these strategies will be readily apparent to one skilled in the art. Using such strategies, and incorporating the mechanisms disclosed herein, the nucleic acid and protein molecules of the invention may be utilized to generate algae, ciliates, plants, fungi or other microorganisms like *C. glutamicum* expressing mutated PKSRP nucleic acid and protein molecules such that the stress tolerance is improved.

The present invention also provides antibodies which specifically bind to a PKSRP-polypeptide, or a portion thereof, as encoded by a nucleic acid disclosed herein or as described herein. Antibodies can be made by many well-known methods (See, e.g. *Harlow and Lane*, "Antibodies; A Laboratory Manual" Cold Spring Harbor Laboratory, Cold Spring Harbor, New York, (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163-167; Bebbington et al., 1992 Bio/Technology 10:169-175).

The phrases "selectively binds" and "specifically binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims. Additionally, all references cited herein are hereby expressly incorporated herein by reference.

EXAMPLES

Example 1

Growth of *Physcomitrella patens* Cultures

For this study, plants of the species *Physcomitrella patens* (Hedw.) B. S. G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol s$^{-1}$ m$^{-2}$ (white light; Philips TL 65 W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation From Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 min using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of H$_2$O+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and poly-(A)+RNA and cDNA Library Construction From *Physcomitrella patens*

For the investigation of transcripts, both total RNA and poly-(A)+RNA were isolated. The total RNA was obtained from wild-type 9 day old protonemata following the GTC-method (Reski et al. 1994, Mol. Gen. Genet., 244:352-359). The Poly(A)+RNA was isolated using Dyna Beads$^R$ (Dynal, Oslo, Norway) following the instructions of the manufacturers protocol. After determination of the concentration of the RNA or of the poly(A)+RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (see Sambrook et al. 1989 Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'      SEQ ID NO:10

5'-CTAAAGGGAACAAAAGCTG-3'     SEQ ID NO:11

5'-TGTAAAACGACGGCCAGT-3'      SEQ ID NO:12
```

Sequences were processed and annotated using the software package EST-MAX commercially provided by Bio-Max (Munich, Germany). The program incorporates practically all bioinformatics methods important for functional and structural characterization of protein sequences. For reference the website at pedant.mips.biochem.mpg.de. The most important algorithms incorporated in EST-MAX are: FASTA: Very sensitive sequence database searches with estimates of statistical significance; Pearson W. R. (1990) Rapid and sensitive sequence comparison with FASTP and FASTA. Methods Enzymol. 183:63-98; BLAST: Very sensitive sequence database searches with estimates of statistical significance. Altschul S. F., Gish W., Miller W., Myers E. W., and Lipman D. J. Basic local alignment search tool. Journal of Molecular Biology 215:403-10; PREDATOR: High-accuracy secondary structure prediction from single and multiple sequences. Frishman, D. and Argos, P. (1997) 75% accuracy in protein secondary structure prediction. Proteins, 27:329-335; CLUSTALW: Multiple sequence alignment. Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680; TMAP: Transmembrane region prediction from multiply aligned sequences. Persson, B. and Argos, P. (1994) Prediction of transmembrane segments in proteins utilizing multiple sequence alignments. J. Mol. Biol. 237:182-192; ALOM2: Transmembrane region prediction from single sequences. Klein, P., Kanehisa, M., and DeLisi, C. Prediction of protein function from sequence properties: A discriminate analysis of a database. Biochim. Biophys. Acta 787:221-226 (1984). Version 2 by Dr. K. Nakai; PROSEARCH: Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919-921; BLIMPS: Similarity searches against a database of ungapped blocks. J. C. Wallace and Henikoff S., (1992); PATMAT: A searching and extraction program for sequence, pattern and block queries and databases, CABIOS 8:249-254. Written by Bill Alford.

Example 5

Identification of *Physcomitrella patens* ORF Corresponding to PpPK-1, PpPK-2 and PpMPK-1

The *Physcomitrella patens* partial cDNAs (ESTs) shown in Table 1 below were identified in the *Physcomitrella patens* EST sequencing program using the program EST-MAX through BLAST analysis. (Tables 2-4 show some of the results). The Sequence Identification Numbers corresponding to these ESTs are as follows: PpPK-1 (SEQ ID NO:1); PpPK-2 (SEQ ID NO:2) and PpMPK-1 (SEQ ID NO:3). These particular clones were chosen for farther analyses since they encoded for protein kinases.

TABLE 1

| Functional Category | Function | Sequence Code | ORF position | Name |
|---|---|---|---|---|
| Protein Kinase | MAP kinase | s_pp004047334r | 1-560 | PpMPK-1 |
| | serine/threonine protein kinase | s_pp004012036r | 1-467 | PpPK-2 |
| | serine/threonine kinase | s_pp004005088r | 1-324 | PpK-1 |

TABLE 2

Degree of Amino Acid Identity and Similarity of PpPK-1 and Other Homologous Proteins (GCG Gap program was used: gap penalty: 10; gap extension penalty: 0.1; score matrix: blosum62)

| Swiss-Prot # | O24342 | Q9ZVD9 | Q9MAM1 | Q9LDI3 | Q9LKC9 |
|---|---|---|---|---|---|
| Protein name | Serine/Threonine kinase | Putative Serine/Threonine protein kinase | T25K16.13 | Serine/Threonine protein kinase SOS2 | CBL-interacting protein kinase 3 |
| Specie | Sorghum bicolor (Sorghum) | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) |
| Identity % | 66% | 62% | 64% | 55% | 55% |
| Similarity % | 78% | 76% | 75% | 69% | 67% |

TABLE 3

Degree of Amino Acid Identity and Similarity of PpPK-2 and Other Homologous Proteins (GCG Gap program was used: gap penalty: 10; gap extension penalty: 0.1; score matrix: blosum62)

| Swiss-Prot # | Q9LZ05 | Q9LZ96 | Q9LJU5 | P43293 | O04245 |
|---|---|---|---|---|---|
| Protein name | Protein kinase-like | Serine/Threonine-specific protein kinase NAK | Receptor protein kinase-like protein | Probable Serine/Threonine-protein kinase NAK | Putative NAK-like Ser/Thr protein kinase |
| Specie | Arabidopsis thaliana (Mouse-ear cress) | Arabidopsi thaliana (Mouse-ear cress) | Arabidopsis thaliana (Mouse-ear cress) | Arabidopsis thaliana (Mouse-ear cress) | Arabidopsis thaliana (Mouse-ear cress) |
| Identity % | 32% | 32% | 32% | 32% | 28% |
| Similarity % | 43% | 41% | 41% | 41% | 35% |

TABLE 4

Degree of Amino Acid Identity and Similarity of PpMPK-1 and Other Homologous Proteins (GCG Gap program was used: gap penalty: 10; gap extension penalty: 0.1; score matrix: blosum62)

| Swiss-Prot # | Q06060 | Q39024 | Q40532 | Q9M136 | Q9M534 |
|---|---|---|---|---|---|
| Protein name | Mitogen-activated protein kinase homolog D5 | Mitogen-activated protein kinase homolog 4 | Mitogen-activated protein kinase homolog NTF4 | MAP kinase 4 | Mitogen-activated protein kinase |
| specie | Pisum sativum (Garden pea) | Arabidopsis thaliana (Mouse-ear cress) | Nicotiana tabacum (Common tobacco) | Arabidopsis thaliana (Mouse-ear cress) | Euphorbi aesula (Leafy spurge) |
| Identity % | 45% | 45% | 44% | 45% | 44% |
| Similarity % | 53% | 52% | 53% | 52% | 53% |

Example 6

Cloning of the Full-Length *Physcomitrella patens* cDNA Encoding for PpPK-1, PpPK-2 and PpMPK-1

To isolate the clones encoding for PpPK-1, PpPk-2 and PpMPK-1 from *Physcomitrella patens*, cDNA libraries were created with SMART RACE cDNA Amplification kit (Clontech Laboratories) following manufacturer's instructions. Total RNA isolated as described in Example 3 was used as the template. The oligos designed for RACE are shown in Table 2. The cultures were treated prior to RNA isolation as follows: Salt Stress: 2, 6, 12, 24, 48 h with 1-M NaCl-supplemented medium; Cold Stress: 4° C. for the same time points as for salt; Drought Stress: cultures were incubated on dry filter paper for the same time points above.

TABLE 5

Scheme and primers used for cloning of full-length clones

| Gene | Final sites in product | Isolation Method | Primers Race | Primer RT-PCR |
|---|---|---|---|---|
| PpPK-1 | XmaI/SacI | 5' RACE and RT-PCR for Full-length clone | RC077 (SEQ ID NO:13) 5'CCGGGCTCCTGACGAGAA CCAAGGA | RC096 (SEQ ID NO:14) 5'ATCCCGGGCGTTCAAGCA GGTGAATATGACAAC |
| | | | | RC097 (SEQ ID NO:15) 3'ATGAGCTCGGGCACTTCA CAGCACGGGCATAT |
| PpPK-2 | XmaI/HpaI | 5' RACE and RT-PCR for Full-length clone | RC051 (SEQ ID NO:15) 5'GCCCCCTTCGCCGACTAC ATTATCA3' | RC156 (SEQ ID NO:16) 5'ATCCCGGGCGCGCACAAT TTCAGTTGGGAATCA |
| | | | | RC157 (SEQ ID NO:17) 5'GCGTTAACGCCCGCAAAG GTCAAAACAGGCGTGG |
| PpMPK-1 | XmaI/HpaI | 5' RACE and RT-PCR for Full-length clone | RC074 (SEQ ID NO:18) 5'GCCGCTGTGTACATTCGG CTCCCAAG | RC100 (SEQ ID NO:19) 5'ATCCCGGGCGGTTTGGAC ACGATGTTCCAGTCC |
| | | | | RC101 (SEQ ID NO:20) 5'GCGTTAACTAACCGCGTT TAAGTCCCTCAAC |

5' RACE Protocol

The EST sequences PpPK-1 (SEQ ID NO:1), PpPK-2 (SEQ ID NO:2) and PpMPK-1 (SEQ ID NO:3) identified from the database search as described in Example 4 were used to design oligos for RACE (see Table 5). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding regions of PpPK-1, PpPK-2 and PpMPK-1 and were used to design oligos for full-length cloning of the respective genes (see below full-length amplification).

Full-length Amplification

Full-length clones of PpPK-1 (SEQ ID NO:4), PpPK-2 (SEQ ID NO:5) and PpMPK-1 (SEQ ID NO:6) were obtained by performing polymerase chain reaction (PCR) with gene-specific primers (see Table 5) and the original EST as the template. The conditions for the reaction were standard conditions with PWO DNA polymerase (Roche). PCR was performed according to standard conditions and to manufacturer's protocols (Sambrook et al. 1989. Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C followed by five cycles of one minute at 94° C., one minute at 50° C. and 1.5 minutes at 72° C. This was followed by twenty five cycles of one minute at 94° C., one minute at 65° C. and 1.5 minutes at 72° C.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al. 1989. Molecular Cloning, A Laboratory Manual. 2nd Edition. Cold Spring Harbor Laboratory Press. Cold Spring Harbor, N.Y.). Transformed cells were selected for on LB agar containing 100 µg/ml carbenicillin, 0.8 mg X-gal (5-bromo4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al. 1989. Molecular Cloning, A Laboratory Manual. 2nd Edition. Cold Spring Harbor Laboratory Press. Cold Spring Harbor, N.Y.).

Example 7

Engineering Stress-Tolerant Arabidopsis Plants by Over-Expressing the Genes PpPK-1, PpPK-2 and PpMPK-1

Binary Vector Construction: pGMSG

The pLMNC53 (Mankin, 2000, PhD thesis) vector was digested with HindIII (Roche) and blunt-end filled with Klenow enzyme and 0.1 mM dNTPs (Roche) according to manufacturer's instructions. This fragment was extracted from agarose gel with a QIAquick Gel Extraction Kit (Qiagen) according to manufacturer's instructions. The purified fragment was then digested with EcoRI (Roche) according to manufacturer's instructions. This fragment was extracted from agarose gel with a QIAquick Gel Extraction Kit (Qiagen) according to manufacturer's instructions. The resulting 1.4 kilobase fragment, the gentamycin cassette, included the nos promoter, aacCI gene and the g7 terminator.

The vector pBlueScript was digested with EcoRI and SmaI (Roche) according to manufacturer's instructions. The resulting fragment was extracted from agarose gel with a QIAquick Gel Extraction Kit (Qiagen) according to manufacturer's instructions. The digested pBlueScript vector and the gentamycin cassette fragments were ligated with T4 DNA Ligase (Roche) according to manufacturer's instructions, joining the two respective EcoRI sites and joining the blunt-ended HindIII site with the SmaI site.

The recombinant vector (pGMBS) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside), grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al. 1989. Molecular Cloning, A Laboratory Manual. 2nd Edition. Cold Spring Harbor Laboratory Press. Cold Spring Harbor, N.Y.).

Both the pGMBS vector and p1bxSuperGUS vector were digested with XbaI and KpnI (Roche) according to manufacturer's instructions, excising the gentamycin cassette from pGMBS and producing the backbone from the p1bxSuperGUS vector. The resulting fragments were extracted from agarose gel with a QIAquick Gel Extraction Kit (Qiagen) according to manufacturer's instructions. These two fragments were ligated with T4 DNA ligase (Roche) according to manufacturer's instructions.

The resulting recombinant vector (pGMSG) was transformed into Top10 cells (Invitrogen) using standard conditions. Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) and grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al. 1989. Molecular Cloning, A Laboratory Manual. 2nd Edition. Cold Spring Harbor Laboratory Press. Cold Spring Harbor, N.Y.).

Subcloning of PpPK-1, PpPK-2 and PpMPK-1 into the Binary Vector

The fragments containing the different *Physcomitrella patens* protein kinase-like genes were subcloned from the recombinant PCR2.1 TOPO vectors by double digestion with restriction enzymes (see Table 6) according to manufacturer's instructions. The subsequence fragment was excised from agarose gel with a QIAquick Gel Extraction Kit (QIAgen) according to manufacturer's instructions and ligated into the binary vector pGMSG, cleaved with appropriate enzymes (see Table 6) and dephosphorylated prior to ligation. The resulting recombinant pGMSG vector contained the corresponding transcription factor in the sense orientation under the control of the constitutive super promoter.

TABLE 6

Names of the various constructs of the *Physcomitrella patens* protein kinase-like proteins used for plant transformation

| Gene | Enzymes used to generate gene fragment | Enzymes used to restrict pGMSG | Binary Vector Construct |
|---|---|---|---|
| PpPK-1 | XmaI/SacI | XmaI/SacI | PBPSLVM004 |
| PpPK-2 | XmaI/HpaI | XmaI/Ec1136 | pBPSLVM005 |
| PpMPK-1 | XmaI/HpaI | XmaI/Ec1136 | PBPSLVM006 |

Agrobacterium Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold 1993, Acad. Sci. Paris. 316:1194-1199; Bent et al. 1994, Science 265:1856-1860).

Screening of Transformed Plants

T1 seeds were sterilized according to standard protocols (Xiong et al. 1999, Plant Molecular Biology Reporter 17: 159-170). Seeds were plated on ½MS 0.6% agar supplemented with 1% sucrose, 150 µg/ml gentamycin (Sigma-Aldrich) and 2 µg/ml benomyl (Sigma-Aldrich). Seeds on plates were vernalized for four days at 4° C. The seeds were germinated in a climatic chamber at an air temperature of 22° C. and light intensity of 40 micromol $s^{-1}$ $m^{-2}$ (white light; Philips TL 65 W/25 fluorescent tube) and 16 hours light and 8 hours dark day length cycle. Transformed seedlings were selected after 14 days and transferred to ½MS 0.6% agar plates supplemented with 1% sucrose and allowed to recover for five-seven days.

Drought Tolerance Screening T1 seedlings were transferred to dry, sterile filter paper in a petri dish and allowed to desiccate for two hours at 80% RH (relative humidity) in a Sanyo Growth Cabinet MLR-350H, micromol $s^{-1}$ $m^{-2}$ (white light; Philips TL 65 W/25 fluorescent tube). The RH was then decreased to 60% and the seedlings were desiccated further for eight hours. Seedlings were then removed and placed on ½MS 0.6% agar plates supplemented with 2 µg/ml benomyl and scored after five days.

The results of the drought tolerance screening in *Arabidopsis thaliana* plants over-expressing the Protein Kinase-like proteins are shown in Table 7. It is noteworthy that these analyses were performed with T1 plants since the results should be better when a homozygous, strong expresser is found.

TABLE 7

Summary of the drought stress tests

Drought Stress Test

| Gene Name | Number of survivors | Total number of plants | Percentage of survivors |
|---|---|---|---|
| PpPK-1 | 2 | 4 | 50% |
| PpPK-2 | 10 | 12 | 84% |

TABLE 7-continued

Summary of the drought stress tests

Drought Stress Test

| Gene Name | Number of survivors | Total number of plants | Percentage of survivors |
|---|---|---|---|
| PpMPK-1 | 23 | 25 | 92% |
| Control | 18 | 84 | 21% |

Salt Tolerance Screening

Seedlings were transferred to filter paper soaked in ½ MS and placed on ½ MS 0.6% agar supplemented with 2 µg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 µg/ml benomyl. The seedlings were scored after 5 days.

The results of the salt tolerance screening in *Arabidopsis thaliana* plants over-expressing the Protein Kinase-like proteins are shown in Table 8. It is noteworthy that these analyses were performed with T1 plants since the results should be better when a homozygous, strong expresser is found.

TABLE 8

Summary of the salt stress tests

Salt Stress Test

| Gene Name | Number of survivors | Total number of plants | Percentage of survivors |
|---|---|---|---|
| PpPK-2 | 5 | 8 | 62% |
| PpMPK-1 | 14 | 25 | 56% |
| Control | 4 | 43 | 9% |

Freezing Tolerance Screening

Seedlings were moved to petri dishes containing ½MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C. decreasing −1° C. each hour. The seedlings were then incubated at −5.0° C. for 24 hours and then allowed to thaw at 5° C. for 12 hours. The water was poured off and the seedlings were scored after 5 days. The transgenic plants are then screened for their improved cold tolerance demonstrating that transgene expression confers cold tolerance.

Example 8

Detection of the PpPK-1, PpPK-2 and PpMPK-1 Transgenes in the Transgenic *Arabidopsis* Lines One leaf from a wild type and a transgenic *Arabidopsis* plant was homogenized in 250 µl Hexadecyltrimethyl ammonium bromide (CTAB) buffer (2% CTAB, 1.4 M NaCl, 8mM EDTA and 20 mM Tris pH 8.0) and 1 µl β-mercaptoethanol. The samples were incubated at 60-65° C. for 30 minutes and 250 µl of Chloroform was then added to each sample. The samples were vortexed for 3 minutes and centrifuged for 5 minutes at 18,000×g. The supernatant was taken from each sample and 150 µl isopropanol was added. The samples were incubated at room temperature for 15 minutes, and centrifuged for 10 minutes at 18,000×g. Each pellet was washed with 70% ethanol, dried, and resuspended in 20 µl TE. 4 µl of above suspension was used in a 20 µl PCR reaction using Taq DNA polymerase (Roche Molecular Biochemicals) according to the manufacturer's instructions. Binary vector plasmid containing each STA gene was used as positive control, and the wild type C24 genomic DNA was used as negative control in the PCR reactions. 10 µl PCR reaction was analyzed on 0.8% agarose-ethidium bromide gel.

Notably, the transgenes were successfully amplified from the T1 transgenic lines, but not from the wild-type C24. This result indicates that the T1 transgenic plants contain at least one copy of the transgenes. There was no indication of existence of either identical or very similar in the untransformed *Arabidopsis thaliana* control which can be amplified by this method.

PpPk-1

The primers used in the reactions were:

```
                                            SEQ ID NO:21
5'CTAGTAACATAGATGACACC3'

SEQ ID NO:22
5' ATCCCGGGCGTTCAAGCAGGTGAATATGACAAC 3'
```

The PCR program was as following: 30 cycles of 1 minute at 94° C., 1 minute at 62° C. and 4 minutes at 72° C., followed by 10 minutes at 72° C. A 1.6 kb fragment was produced from the positive control and the transgenic plants.

PpPk-2

The primers used in the reactions were:

```
                                            SEQ ID NO:23
5'GAATAGATACGCTGACACGC3'

SEQ ID NO:24
5'GCGTTAACGCCCGCAAAGGTCAAAACAGGCGTGG3'
```

The primers were used in the first round of reactions with the following program: 30 cycles of 1 minute at 94° C., 1 minute at 62° C. and 4 minutes at 72° C., followed by 10 minutes at 72° C. Then 1 µl of above reaction was reamplified in a 20 µl reaction using the following primers in the same program:

```
                                            SEQ ID NO:25
5'ATCCCGGGCGCGCACAATTTCAGTTGGGAATCA3'

SEQ ID NO:24
5'GCGTTAACGCCCGCAAAGGTCAAAACAGGCGTGG3'
```

A 2.0 kb fragment was generated from the positive control and the T1 transgenic plants.

PpMPK-1

The primers used in the reactions were:

```
                                            SEQ ID NO:26
5'ATCCCGGGCGGTTTGGACACGATGTGTTCCAGTCC3'

SEQ ID NO:27
5'GCGTTAACTAACCGCGTTTAAGTCCCTCAAC3'
```

The PCR program was as following: 30 cycles of 1 minute at 94° C., 1 minute at 62° C. and 4 minutes at 72° C., followed by 10 minutes at 72° C. A 1.6 kb fragment was produced from the positive control and the transgenic plants.

Example 9

Detection of the PpPK-1, PpPK-2 and PpMPK-1 Transgene mRNA in Transgenic *Arabidopsis* Lines Transgene expression was detected using RT-PCR. Total RNA was isolated from stress-treated plants using a procedure adapted from (Verwoerd et al. 1989. NAR 17:2362). Leaf samples (50-100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding $\frac{1}{10}^{th}$ volume 3M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 µl DEPC treated water. To remove contaminating DNA from the samples, each was treated with RNase-free DNase (Roche) according to the manufacturer's recommendations. cDNA was synthesized from total RNA using the $1^{st}$ Strand cDNA synthesis kit (Boehringer Mannheim) following manufacturer's recommendations. PCR amplification of a gene-specific fragment from the synthesized cDNA was performed using Taq DNA polymerase (Roche) and gene-specific primers (see Table 5 for primers) in the following reaction: 1×PCR buffer, 1.5 mM $MgCl_2$, 0.2 µM each primer, 0.2 µM dNTPs, 1 unit polymerase, 5 µl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 7.

Example 10

Engineering Stress-Tolerant Soybean Plants by Over-Expressing the PpPK-1, PpPK-2 and PpMPK-1 Gene The constructs pBPSLVM004, pBPSLVM005 and pBPSLVM006 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacterial culture is pelleted at 7000 rpm for 7 minutes at room temperature, and resuspended in MS (Murashige and Skoog, 1962) medium supplemented with 100 μM acetosyringone. Bacterial cultures are incubated in this pre-induction medium for 2 hours at room temperature before use. The axes of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated for 4 weeks at 25° C., under 150 μmol m$^{-2}$ sec$^{-1}$ and 12 hours photoperiod. Once the seedlings produced roots, they are transferred to sterile metromix soil. The medium of the in vitro plants is washed off before the plants are transferred to soil. The plants are kept under a plastic cover for 1 week to favor the acclimatization process. Then the plants are transferred to a growth room where they are incubated at 25° C., under 150 μmol m$^{-2}$ sec$^{-1}$ light intensity and 12 hours photoperiod for about 80 days.

The transgenic plants are then screened for their improved drought, salt andlor cold tolerance according to the screening method described in Example 7 to demonstrate that transgene expression confers stress tolerance.

Example 11

Engineering Stress-Tolerant Rapeseed/Canola Plants by Over-Expressing the PpPK-1, PpPK-2 and PpMPK-1 Gene The constructs pBPSLVM004, pBPSLVM005 and pBPSLVM006 are used to transform rapeseed/canola as described below.

The method of plant transformation described herein is also applicable to Brassica and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approx. 85% of its water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7 to demonstrate that transgene expression confers drought tolerance.

Example 12

Engineering Stress-Tolerant Corn Plants by Over-Expressing the PpCABF-1; PpDBF-1, PpCBF-1, PpHDZ-1, PpZF-1, PpLZ-1 and PpCABF-2 Gene The constructs pBPSLVM004, pBPSLVM005 and pBPSLVM006 are used to transform corn as described below.

Transformation of maize (*Zea Mays L.*) is performed with the method described by Ishida et al., 1996 Nature Biotch 14745-50. Immature embryos are co-cultivated with *Agrobacterium tumefaciens* that carry "super binary" vectors, and trangenic plants are recovered through organogenesis. This procedure provides a tranformation efficiency of between 2.5% and 20%. The transgenic plants are then screened for their improved drought, salt and/or cold tolerance according to the screening method described in Example 7 to demonstrate that transgene expression confers stress tolerance.

Example 13

Engineering Stress-Tolerant Wheat Plants by Over-Expressing the PpPK-1, PpPK-2 and PpMPK-1 Gene The constructs The constructs pBPSLVM004, pBPSLVM005 and pBPSLVM006 are used to transform wheat as described below.

Transformation of wheat is performed with the method described by Ishida et al., 1996 Nature Biotch 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 to demonstrate that transgene expression confers drought tolerance.

Example 15

Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example EDNA libraries. Depending on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. In aqueous solution hybridization and washing is performed at an ionic strength of 1 M NaCl and a temperature of 68° C. Hybridization probes are generated by e.g. radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide hybridization solution:
6×SSC
0.01 M sodium phosphate
1 mM EDTA (pH 8)
0.5% SDS
100 µg/ml denatured salmon sperm DNA
0.1% nonfat dried milk During hybridization, temperature is lowered stepwise to 5-10° C. below the estimated oligonucleotide Tm or down to room temperature followed by washing steps and autoradiography. Washing is performed with low stringency such as 3 washing steps using 4×SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 16

Identification of Homologous Genes by Screening Expression Libraries with Antibodies c-DNA clones can be used to produce recombinant protein for example in *E. coli* (e.g. Qiagen QIAexpress pQE system). Recombinant proteins are then normally affinity purified via Ni—NTA affinity chromatography (Qiagen). Recombinant proteins are then used to produce specific antibodies for example by using standard techniques for rabbit immunization. Antibodies are affinity purified using a Ni—NTA column saturated with the recombinant antigen as described by Gu et al., 1994 BioTechniques 17:257-262. The antibody can than be used to screen expression cDNA libraries to identify homologous or heterologous genes via an immunological screening (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons).

Example 17

In vivo Mutagenesis

In vivo mutagenesis of microorganisms can be performed by passage of plasmid (or other vector) DNA through *E. coli* or other microorganisms (e.g. Bacillus spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella*, p. 2277-2$^{29}$$^4$, ASM: Washington.) Such strains are well known to those skilled in the art. The use of such strains is illustrated, for example, in Greener, A. and Callahan, M. (1994) *Strategies* 7: 32-34. Transfer of mutated DNA molecules into plants is preferably done after selection and testing in microorganisms. Transgenic plants are generated according to various examples within the exemplification of this document.

Example 18

In vitro Analysis of the Function of Physcomitrella Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, 3$^{rd}$ ed. Academic Press: New York; Bisswanger, H., (1994) Enzymkinetik, 2$^{nd}$ ed. VCH: Weinheim (ISBN 3527300325); Bergmeyer, H. U., Bergmeyer, J., Graβl, M., eds. (1983-1986) Methods of Enzymatic Analysis, 3$^{rd}$ ed., vol. I-XII, Verlag Chemie: Weinheim; and Ullmann's Encyclopedia of Industrial Chemistry (1987) vol. A9, Enzymes. VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) *EMBO J.* 14: 3895-3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B. Pores, Channels and Transporters, in Biomembranes, Molecular Structure and Function, pp. 85-137, 199-234 and 270-322, Springer: Heidelberg (1989).

Example 19

Purification of the Desired Product from Transformed Organisms

Recovery of the desired product from plant material (i.e., *Physcomitrella patents* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonication. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be Well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 Appl. Environ. Microbiol. 60:133-140; Malakhova et al., 1996 Biotekhnologiya 11:27-32; and Schmidt et al., 1998 Bioprocess Engineer. 19:67-70. Ulmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

---

We claim:

1. An isolated nucleic acid comprising a polynucleotide encoding a polypeptide as defined in SEQ ID NO:9.

2. A method of producing a transgenic plant comprising a nucleic acid encoding a polypeptide, wherein expression of the nucleic acid in the plant results in the plant having increased tolerance to drought and/or salt stress as compared to an untransformed wild type variety of the plant, the method comprising the steps of:
   a) transforming a plant cell with an expression vector comprising the nucleic acid; and
   b) generating from the plant cell a transgenic plant;
   wherein the nucleic acid is selected from the group consisting of:
   i) a polynucleotide encoding a polypeptide as defined in SEQ ID NO:9; and
   ii) a polynucleotide as defined in SEQ ID NO:6.

3. The method of claim 2, wherein the nucleic acid comprises the polynucleotide encoding the polypeptide as defined in SEQ ID NO:9.

4. The method of claim 2, wherein the plant is a monocot.

5. The method of claim 2, wherein the plant is a dicot.

6. The method of claim 2, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, and perennial grass and a forage crop plant.

7. A method of modifying stress tolerance of a plant comprising the step of transfecting an isolated nucleic acid in the plant, wherein expression of the nucleic acid in the plant results in increased tolerance to drought or salt stress as compared to an untransformed wild type variety of the plant, wherein the nucleic acid is selected from the group consisting of:
   a) a polynucleotide encoding a polypeptide as defined in SEQ ID NO9 and
   b) a polynucleotide as defined in SEQ ID NO:6.

8. The method of claim 7, wherein the nucleic acid comprises the polynucleotide encoding the polypeptide as defined in SEQ ID NO:9.

9. The method of claim 7, wherein the plant is a monocot.

10. The method of claim 7, wherein the plant is a dicot.

11. The method of claim 7, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, and perennial grass and a forage crop plant.

12. The method of claim 11, wherein the plant is corn.

13. The method of claim 11, wherein the plant is soybean.

14. The method of claim 11, wherein the plant is rapeseed or canola.

15. The method of claim 11, wherein the plant is cotton.

16. An isolated nucleic acid comprising a polynucleotide as defined in SEQ ID NO:6.

17. The method of claim 2, wherein the nucleicacid comprises the polynucleotide as defined in SEQ ID NO:6.

18. The method of claim 7, wherein the nucleic acid comprises the polynucleotide as defined in SEQ ID NO:6.

* * * * *